US011612651B2

(12) United States Patent
Beaudoin

(10) Patent No.: US 11,612,651 B2
(45) Date of Patent: Mar. 28, 2023

(54) STEROID ACID-BASED IMMUNOGEN ENHANCERS

(71) Applicant: DEFENCE THERAPEUTICS INC., Vancouver (CA)

(72) Inventor: Simon Beaudoin, Sherbrooke (CA)

(73) Assignee: DEFENCE THERAPEUTICS INC., Vancouver (CA)

( * ) Notice: Subject to any disclaimer, the term of this patent is extended or adjusted under 35 U.S.C. 154(b) by 0 days.

(21) Appl. No.: 17/738,548

(22) Filed: May 6, 2022

(65) Prior Publication Data

US 2022/0354948 A1 Nov. 10, 2022

Related U.S. Application Data

(60) Provisional application No. 63/362,494, filed on Apr. 5, 2022, provisional application No. 63/201,620, filed on May 6, 2021.

(51) Int. Cl.
| | | |
|---|---|---|
| *A61K 47/50* | (2017.01) |
| *A61P 31/14* | (2006.01) |
| *A61K 39/385* | (2006.01) |
| *A61K 47/54* | (2017.01) |
| *A61K 47/64* | (2017.01) |
| *A61K 39/00* | (2006.01) |

(52) U.S. Cl.
CPC .......... *A61K 39/385* (2013.01); *A61K 47/542* (2017.08); *A61K 47/554* (2017.08); *A61K 47/64* (2017.08); *A61P 31/14* (2018.01); *A61K 2039/6006* (2013.01); *A61K 2039/6031* (2013.01)

(58) Field of Classification Search
None
See application file for complete search history.

(56) References Cited

U.S. PATENT DOCUMENTS 11,291,717 B1 4/2022 Beaudoin

FOREIGN PATENT DOCUMENTS

| WO | 2017/156630 | 9/2017 | | |
|---|---|---|---|---|
| WO | 2018/165752 | 9/2018 | | |
| WO | WO2020/252298 | * | 6/2020 | ............. A61K 38/10 |

OTHER PUBLICATIONS

El-Kadiry et al., "Accum™ Technology: A Novel Conjugable Primer for Onco-Immunotherapy," *Molecules* 27:(3807), 13 pages (2022).
International Search Report for PCT/CA2022/050714, dated Aug. 9, 2022, 6 pages.
Written Opinion of the International Searching Authority for PCT/CA2022/050714, dated Aug. 9, 2022, 6 pages.
Al-Hilal et al., "Functional transformations of bile acid transporters induced by high-affinity macromolecules," *Scientific Reports* 4:4163, 9 pages (2014).
Anding et al., "Cleaning House: Selective Autophagy of Organelles," *Developmental Cell* 41:10-22 (2017).
Anguille et al., "Clinical use of dendritic cells for cancer therapy," *Lancet Oncology* 15:e257-e267 (2014).
Azuar et al., "Cholic Acid-based Delivery System for Vaccine Candidates against Group A Streptococcus," *ACS Med. Chem. Lett.* 70:1253-1259 (2019).
Beaudoin et al., "ChAcNLS, a Novel Modification to Antibody-Conjugates Permitting Target Cell-Specific Endosomal Escape, Localization to the Nucleus, and Enhanced Total Intracellular Accumulation," *Mol. Pharmaceutics* 13:1915-1926 (2016).
Beaudoin et al., "Initial Evaluation of Antibody-conjugates Modified with Viral-derived Peptides for Increasing Cellular Accumulation and Improving Tumor Targeting," *Journal of Visualized Experiments* 133:e55440, 14 pages, (2018).
Beck et al., "Strategies and challenges for the next generation of antibody-drug conjugates," *Nature Reviews | Drug Discovery* 16:315-331 (2017).
Hanafi et al., "Overview of Bile Acids Signaling and Perspective on the Signal of Ursodeoxycholic Acid, the Most Hydrophilic Bile Acid, in the Heart," *Biomolecules* 8:159, 19 pages (2018).
Lacasse et al., "A Novel Proteomic Method Reveals NLS Tagging of T-DM1 Contravenes Classical Nuclear Transport in a Model of HER2-Positive Breast Cancer," *Molecular Therapy: Methods & Clinical Development* 19:99-119 (2020).
Linke et al., "Stimulation of Acid Sphingomyelinase Activity by Lysosomal Lipids and Sphingolipid Activator Proteins," *Biol. Chem.* 382:283-290 (2001).
Liu et al. "The Renpenning syndrome-associated protein PQBP1 facilitates the nuclear import of splicing factor TXNL4 A through the karyopherin β2 receptor," *J. Biol. Chem.* 295(13):4093-4100 (2020).
Murakami et al., "Bile acids and ceramide overcome the entry restriction for GII.3 human norovirus replication in human intestinal enteroids," *PNAS* 117(3):1700-1710 (2020).
Paquette et al., "NLS-Cholic Acid Conjugation to IL-5Rα-Specific Antibody Improves Cellular Accumulation and In Vivo Tumor-Targeting Properties in a Bladder Cancer Model," *Bioconjugate Chem.* 29:1352-1363 (2018).
Patel et al., "Next generation approaches for tumor vaccination," *Chin Clin Oncol* 6(2):19, 12 pages (2017).
Shivanna et al., "The crucial role of bile acids in the entry of porcine enteric calicivirus," *Virology* 456-457:268-218 (2014).

(Continued)

*Primary Examiner* — Agnieszka Boesen
(74) *Attorney, Agent, or Firm* — Seed IP Law Group LLP

(57) ABSTRACT

Immunogen enhancers for admixture with an antigen of interest are described herein. The enhancers generally comprise a steroid acid and/or a steroid acid-peptide conjugate in an amount sufficient to improve or modify the adaptive immune response to antigens admixed therewith. In embodiments, the steroid acid may be a bile acid and the peptide may comprise one or more functional domains, such as a nuclear localization signal, which may facilitate antigen-presentation and/or antigen cross-presentation, thereby triggering improved cellular immunity, or improved cellular and humoral immunity, against the antigen.

20 Claims, 10 Drawing Sheets

Specification includes a Sequence Listing.

(56) References Cited

OTHER PUBLICATIONS

Shivanna et al., "Ceramide Formation Mediated by Acid Sphingomyelinase Facilitates Endosomal Escape of Caliciviruses," *Virology* 483:218-228 (2015).
Smith et al., "Alternative tumour-specific antigens," *Nature Reviews | Cancer* 19:465-478 (2019).
Sun et al., "Factors influencing the nuclear targeting ability of nuclear localization signals," *Journal of Drug Targeting* 24(10):927-933 (2016).
Swaan et al., "Enhanced Transepithelial Transport of Peptides by Conjugation to Cholic Acid," *Bioconjugate Chem.* 8:520-525 (1997).
Tagliamonte et al., "Antigen-specific vaccines for cancer treatment," *Human Vaccines & Immunotherapeutics* 10(11):332-3346 (2014).

\* cited by examiner

| SAMPLE | OVA$^{647}$ (MFI) |
|---|---|
| CA-NLS1 RPS17 + OVA$^{647}$ (22:1) | 1625 |
| CA-NLS1 RPS17 + OVA$^{647}$ (12:1) | 1496 |
| CA-NLS1 RPS17 + OVA$^{647}$ (8:1) | 1861 |
| CA-NLS1 RPS17 + OVA$^{647}$ (4:1) | 2005 |
| CA-NLS1 RPS17 + OVA$^{647}$ (2:1) | 1075 |
| OVA$^{647}$ alone | 774 |
| MSCs alone | 19.2 |

| SAMPLE | OVA$^{647}$ (MFI) |
|---|---|
| CA-NLS3 RPS17 + OVA$^{647}$ (22:1) | 2359 |
| CA-NLS3 RPS17 + OVA$^{647}$ (12:1) | 5804 |
| CA-NLS3 RPS17 + OVA$^{647}$ (8:1) | 5381 |
| CA-NLS3 RPS17 + OVA$^{647}$ (4:1) | 5517 |
| CA-NLS3 RPS17 + OVA$^{647}$ (2:1) | 5102 |
| OVA$^{647}$ alone | 774 |
| MSCs alone | 19.2 |

| SAMPLE | OVA$^{647}$ (MFI) |
|---|---|
| CA-PQBP-1 + OVA$^{647}$ (22:1) | 2475 |
| CA-PQBP-1 + OVA$^{647}$ (12:1) | 1705 |
| CA-PQBP-1 + OVA$^{647}$ (8:1) | 1061 |
| CA-PQBP-1 + OVA$^{647}$ (4:1) | 734 |
| CA-PQBP-1 + OVA$^{647}$ (2:1) | 808 |
| OVA$^{647}$ alone | 774 |
| MSCs alone | 19.2 |

| SAMPLE | OVA$^{DQ}$ (MFI) |
|---|---|
| CA-PQBP-1 + OVA$^{DQ}$ (22:1) | 7148 |
| CA-PQBP-1 + OVA$^{DQ}$ (12:1) | 5771 |
| CA-PQBP-1 + OVA$^{DQ}$ (8:1) | 5972 |
| CA-PQBP-1 + OVA$^{DQ}$ (4:1) | 2819 |
| CA-PQBP-1 + OVA$^{DQ}$ (2:1) | 1504 |
| OVA$^{DQ}$ alone | 1100 |
| MSCs alone | 64.9 |

STEROID ACID-BASED IMMUNOGEN ENHANCERS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 250118_401_SEQUENCE_LISTING.txt. The text file is 4,553 bytes, was created on May 6, 2022, and is being submitted electronically via EFS-Web.

The present description relates to methods of enhancing immunogenicity of antigens. More specifically, the present description relates to steroid acid and steroid acid-peptide conjugates for improving antigen immunogenicity.

BACKGROUND

While subunit vaccines are generally considered amongst the safest vaccines, such antigens may not elicit sufficiently strong immune responses to provide protective and long-lasting immunity. Thus, methods of improving the immunogenicity and efficacy of subunit vaccines would be highly desirable.

SUMMARY

In a first aspect, described herein is an immunogenic composition comprising an antigen admixed with an enhancer of antigen-presentation, the enhancer comprising a steroid acid and/or a steroid acid-peptide conjugate in an amount sufficient to improve presentation of the antigen upon administration of the composition to antigen-presenting cells, as compared to administration of a corresponding composition lacking the enhancer. In embodiments, the steroid acid may be a bile acid or bile acid analog, and the peptide may comprise a functional domain such as a nuclear localization signal, endosome escape signal, and/or protein transduction domain.

In a further aspect, described herein is a cell culture comprising a population of cells and an immunogenic composition as described herein. In a further aspect, described herein is a vaccine comprising an immunogenic composition as described herein, or comprising cells produced using the cell culture as described herein. In a further aspect, described herein is a method for triggering an enhanced adaptive immune response in a subject against an antigen of interest, the method comprising administering to the subject a composition as described herein, or cells produced using the cell culture as described herein.

In a further aspect, described herein are steroid acid-peptide conjugates for use in admixture with an antigen to enhance immunogenicity, or for use in the manufacture of a medicament for generating an immune response in a subject.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

Other objects, advantages and features of the present description will become more apparent upon reading of the following non-restrictive description of specific embodiments thereof, given by way of example only with reference to the accompanying drawings.

SEQUENCE LISTING

Figure 1:
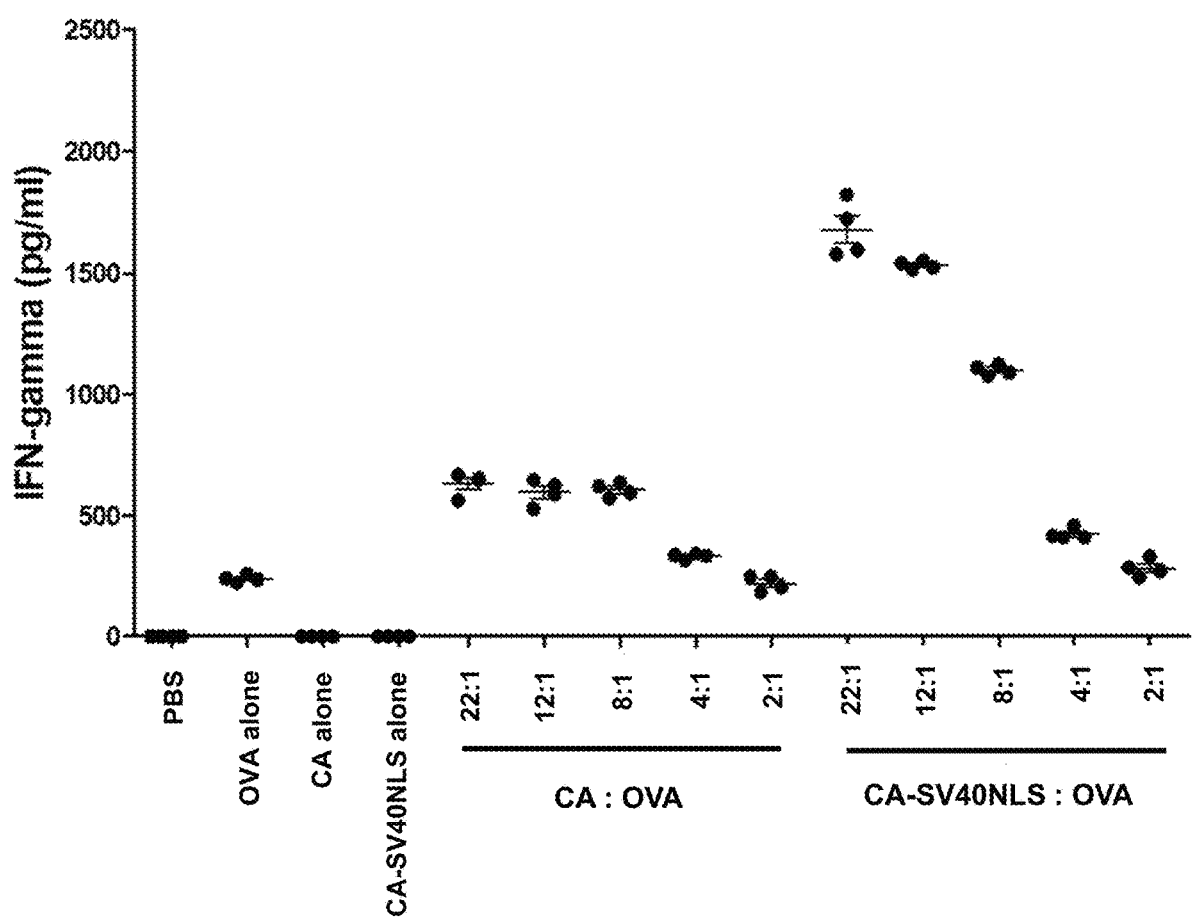
FIG. 1 shows the results of an antigen cross-presentation assay with bone marrow-derived dendritic cells (BMDCs) to assess OVA-responding OT-I (CD8) cells. Mouse BMDCs were pulsed for 3 hours with antigen (OVA) alone, cholic acid (CA) alone, a cholic acid-NLS peptide conjugate (CA-SV40NLS) alone, different ratios of CA to antigen (CA:OVA=22:1, 12:1, 8:1, 4:1, and 2:1), or different ratios of an cholic acid-NLS peptide conjugate to antigen (CA-SV40NLS:OVA=22:1, 12:1, 8:1, 4:1, and 2:1). The pulsed BMDCs were then co-cultured with OT-I mouse-derived CD8 T-cells and IFN-gamma levels were quantified as a measure of cross presentation activity.

This application contains a Sequence Listing in computer readable form created May 5, 2022. The computer readable form is incorporated herein by reference.

TABLE 1

Sequence Listing Description

| SEQ ID NO: | Description |
| --- | --- |
| 1 | SV40NLS |
| 2 | Nuclear localization signal from SV40 large T-antigen |
| 3 | GWG-SV40NLS |
| 4 | hnRNPA1 M9 NLS |
| 5 | hnRNP D NLS |
| 6 | PQBP-1 NLS |
| 7 | NLS2 RPS17 |
| 8 | NLS3 RPS17 |
| 9 | SIINFEKL peptide |
| 10 | hnRNP M NLS |
| 11 | NLS2-RG Domain RPS17 |
| 12 | cMyc NLS |
| 13 | HuR NLS |
| 14 | Tus NLS |
| 15 | NLS1 RPS17 |
| 16 | Nucleoplasmin NLS |

DETAILED DESCRIPTION

Described herein are compositions, cells, and methods relating to improving or modifying the adaptive immune response to antigens. In some aspects, the present invention stems from the demonstration herein that admixture of an antigen with a steroid acid or a steroid acid-peptide conjugate improves antigen-presentation and/or triggers improved cellular immunity, or improved cellular and humoral immunity, against the antigen. In some embodiments, described herein is the use of steroid acids or steroid acid-peptide conjugates as enhancers of antigen-presentation and/or adaptive immunity. Advantageously, the enhancers described herein are not covalently conjugated to antigens, thereby providing a versatile platform rapidly adaptable for formulation with different antigens at enhancer: antigen molar ratios tailorable to the antigen of interest.

In a first aspect, described herein is a composition comprising an antigen admixed with an enhancer of antigen-presentation. As used herein, the term "admixture" or "admixing" refers to the combination of two separate components into a single composition, wherein the components are not covalently conjugated or otherwise reacted together. In some embodiments, the enhancer may comprise a steroid acid in an amount sufficient to improve presentation of the antigen upon administration of the composition to antigen-presenting cells (e.g., in vitro, ex vivo, or in vivo), as compared to administration of a corresponding composition lacking the enhancer. In some embodiments, the enhancer may comprise a steroid acid-peptide conjugate in an amount sufficient to improve presentation of the antigen upon administration of the composition to antigen-presenting cells (e.g., in vitro, ex vivo, or in vivo), as compared to administration of a corresponding composition lacking the enhancer.

Polypeptide antigens are normally captured by antigen-presenting cells (e.g., dendritic cells) but are initially entrapped in endosomes. Endosomal maturation towards lysosomes results in a decrease in pH and an activation of proteolytic enzymes that mediate non-specific antigen degradation. As a result, some of the antigen fragments generated may then pass through endosomal pores to reach the cytosol where further antigen degradation takes place by the proteasomal machinery prior to MHC class I presentation. Although this process occurs naturally, the generated antigen fragments that ultimately leave the endosomes may be small and/or damaged, rendering them unsuitable for proteasomal degradation, thereby precluding their MHC class I presentation and thus cellular immunity based thereon. Without being bound by theory, admixture of antigens with immunogen enhancers described herein may facilitate internalization/endosomal escape of the antigens, allowing them (or larger antigen fragments) to reach the cytosol in a more native conformation and/or in greater quantities. As a result, proteasomal degradation of these more native antigens may result in a higher amount and/or variety of immunogenic and/or stable peptides presented via MHC class I at the surface of antigen-presenting cells, thereby eliciting potent T-cell activation.

In some embodiments, the steroid acid described herein (e.g., in the enhancer and/or in the steroid acid-peptide conjugate) may be a steroid acid that enhances endocytosis and/or endosomal escape of internalized cargoes. Without being bound by theory, steroid acids (e.g., bile acids and bile acid analogs) have been shown to be utilized/exploited by viruses to facilitate their infection of host cells, such as by increasing their endocytic uptake and/or endosomal escape to gain access to the cytosol (Shivanna et al., 2014; Shivanna et al., 2015; Murakami et al., 2020). For example, bile acids have been shown to trigger the enzyme acid sphingomyelinase (ASM) to cleave sphingomyelin to ceramide on the inner leaflet of endosomes. Increased amounts of ceramide destabilize membranes and facilitate endosomal escape. In some embodiments, steroid acids described herein may comprise those that trigger ceramide accumulation on the inner leaflet of endosomes, thereby destabilizing endosomal membranes and facilitating endosomal escape of the modified polypeptide antigen upon intracellular delivery. In some embodiments, steroid acids described herein may comprise those that trigger increased acid sphingomyelinase (ASM)-mediated cleavage of sphingomyelin to form ceramide.

In some embodiments, the steroid acid described herein may be a bile acid, such as a primary bile acid or a secondary bile acid. In some embodiments, the steroid acid described herein may be a bile acid oligomer comprising one or more bile acid moieties (Al-Hilal et al., 2014). In some embodiments, the steroid acid described herein may be or comprise a bile acid which is: cholic acid (CA), chenodeoxycholic acid (CDCA), deoxycholic acid (DCA), lithocholic acid (LCA), glycocholic acid (GCA), taurocholic acid (TCA), glycodeoxycholic acid (GDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA). In some embodiments, the steroid acid described herein may be or comprise: glycodeoxycholic acid (GDCA), glycochenodeoxycholic acid (GCDCA), ursodeoxycholic acid (UDCA), lithocholic acid (LCA), or an analog thereof that enhances antigen-presentation and/or adaptive immunity against an antigen when employed in an enhancer described herein. In some embodiments, the steroid acid described herein may be or comprise an analog of a bile acid described herein that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid.

Hydrophobic bile acids such as GCDCA, TCA, GCA, and CA (but not hydrophilic bile acids such as UDCA) were shown to increase GII.3 human norovirus infection and replication in host intestinal cells by enhancing endosomal uptake and endosomal escape via ASM-mediated ceramide accumulation on the apical membrane (Murakami et al., 2020). In some embodiments, steroid acids described herein may comprise or consist of a bile acid or bile acid analog that is more hydrophobic than cholic acid. In some embodiments, a steroid acid suitable for conjugation to a polypeptide antigen described herein comprises or consists of a bile acid or bile acid analog that is more hydrophobic than cholic acid (e.g., CDCA, DCA, LCA, TCA, TDCA, TCDCA, GCA, GDCA, or GCDCA; Hanafi et al., 2018).

In some embodiments, the peptide comprised in a steroid acid-peptide conjugate described herein may comprise one or more domains imparting a desired functionality to the conjugate (e.g., subcellular targeting, nuclear localization, nucleolar localization, endosomal escape, and/or protein transduction), which may further enhance immunogenicity. As used herein, a "domain" generally refers to a part of a protein having a particular functionality. Some domains conserve their function when separated from the rest of the protein, and thus can be used in a modular fashion. The modular characteristic of many protein domains can provide flexibility in terms of their placement within the peptides described herein. However, some domains may perform better when engineered at certain positions of the peptide (e.g., at the N- or C-terminal region, or therebetween). The position of the domain within its endogenous protein may be an indicator of where the domain should be engineered within the peptide.

In some embodiments, the peptide may comprise a subcellular targeting signal promoting targeting of the modified polypeptide antigen to a specific subcellular compartment. In some embodiments, the peptides described herein may comprise a nuclear localization signal (NLS). In some embodiments, the NLS described herein may comprise a classical NLS (e.g., comprising a K-K/R-X-K/R motif), a PY-NLS (e.g., comprising one or more PY motifs, such as towards the C-terminal end of the NLS), a PL-NLS (e.g., comprising one or more PL motifs, such as towards the C-terminal end of the NLS), a ribosomal NLS, an NLS further comprising a nucleolar targeting signal, or any combination thereof.

In some embodiments, the NLS described herein may comprise the general consensus sequence: (i) K(K/R)X(K/R); (ii) (K/R)(K/R)X$_{10-12}$(K/R)$_{3/5}$, wherein (K/R)$_{3/5}$ represents three lysine or arginine residues out of five consecutive amino acids; (iii) KRX$_{10-12}$KRRK; (iv) KRX$_{10-12}$K(K/R)(K/R); or (v) KRX$_{10-12}$K(K/R)X(K/R), wherein X is any amino acid (Sun et al., 2016).

In some embodiments, the NLS described herein may be a hydrophobic and/or basic NLS. In some embodiments, the NLS describe herein may comprise at least three, four, or five acidic residues (e.g., R/K) and/or at least three, four or five basic residues (e.g., E/D).

In some embodiments, the NLS described herein may be or be derived from the NLS from SV-40 large T-antigen (e.g., SV40 NLS), a c-Myc NLS, an acidic M9 domain in the hnRNP A1 protein (e.g., hnRNPA1 M9 NLS), an hnRNP D NLS, an hnRNP M NLS, a PQBP-1 NLS, an HuR NLS, Tus NLS, Nucleopasmin NLS, NLS1 RPS17, NLS2 RPS17, NLS3 RPS17, or NLS2-RG domain RSP17.

In some embodiments, the nuclear localization signals described herein may comprise or be derived from the NLS from SV-40 large T-antigen (e.g., PKKKRKV; SEQ ID NO: 1 or 2) or from other classical NLSs. In some embodiments, the nuclear localization signals described herein may comprise or be derived from non-classical NLS (e.g., acidic M9 domain in the hnRNP A1 protein; the sequence KIPIK in yeast transcription repressor Matα2; PY-NLS; ribosomal NLS; or the complex signals of U snRNPs). In some embodiments, the nuclear localization signal described herein comprises or consists essentially of the amino acid sequence of any one of SEQ ID NOs: 1 to 8 or 10 to 16, or any portion thereof. In some embodiments, the nuclear localization signal described herein comprises or consists essentially of a nuclear localisation signal which is SV40 NLS (e.g., comprised in SEQ ID NO: 1 or 2), GWG-SV40 NLS (e.g., comprised in SEQ ID NO: 3), hnRNPA1 M9 NLS (e.g., comprised in SEQ ID NO: 4), hnRNP D NLS (e.g., comprised in SEQ ID NO: 5), hnRNP M NLS (e.g., comprised in SEQ ID NO: 10), PQBP-1 NLS (e.g., comprised in SEQ ID NO: 6), NLS2-RG Domain RPS17 (e.g., comprised in SEQ ID NO: 11), NLS1 RPS17 (e.g., comprised in SEQ ID NO: 15), NLS2 RPS17 (e.g., comprised in SEQ ID NO: 7), NLS3 RPS17 (e.g., comprised in SEQ ID NO: 8), cMyc NLS (e.g., comprised in SEQ ID NO: 12), HuR NLS (e.g., comprised in SEQ ID NO: 13), Tus NLS (e.g., comprised in SEQ ID NO: 14), or Nucleoplasmin NLS (e.g., comprised in SEQ ID NO: 16). In some instances, the SEQ ID NOs referred to above comprise an N-terminal cysteine residue that was used to facilitate conjugation to the polypeptide antigen (e.g., the thiol group of the N-terminal cysteine residue). Thus, in some embodiments, the NLS sequences referred to herein may exclude the N-terminal cysteine residue comprised in any one of SEQ ID NOs: 1 to 8 or 10 to 16. In some embodiments, other functional groups added or inserted (e.g., towards the N to C terminal portions of the peptides described herein) to facilitate steroid acid-peptide conjugation to a given polypeptide antigen are also envisaged (e.g., carboxyl groups, synthetic amino acids, etc.). For example, the peptide may include a C-term amide and/or an N-term cysteine. In some embodiments, peptide does not comprise an endosomal escape motif, or protein transduction, or cell penetrating motif.

In some embodiments, the NLS described herein may be a PQBP-1 NLS (e.g., comprising at least residues 3 to 21 of SEQ ID NO: 6) or another NLS that binds to nuclear import receptor Kapβ2. In some embodiments, the NLS described herein may comprise the motif R-X$_{2-5}$-PY that was found to be necessary for PQBP-1 binding to Kapβ2 (Liu et al., 2020).

In some embodiments, the NLS described herein may comprise an endosomolytic motif that facilitates endosomal escape of the antigen upon internalization into an antigen-presenting cell. In some embodiments, the NLS described herein may comprise a protein transduction domain that stimulates endocytosis and/or endosomal formation, thereby facilitating internalization into an antigen-presenting cell. In some embodiments, the NLS described herein may lacks a protein transduction domain or cell penetrating peptide, which may be advantageous to avoid triggering more rapid internalization of the steroid acid-conjugate as compared to the antigen.

In some embodiments, the peptide described herein may comprise a protein transduction domain (PTD) that stimulates endocytosis, endosomal formation, or intracellular delivery in a non-cell-specific manner.

In some embodiments, the peptide is preferably a non-immunogenic peptide, thereby favoring immune responses generated against the antigen of interest instead of against the peptide in the steroid acid-peptide conjugate enhancer. For example, Azuar et al., 2019 conjugated cholic acid to an antigenic peptide derived from Group A *Streptococcus*, which reportedly self-assembled into rod-like nanoparticles and triggered stronger humoral immune responses against the antigenic peptide. Such humoral immune responses against the enhancers described herein are not desirable.

In some embodiments, the peptide described herein may have a length of at least 7, 8, 9, 10, 11, or 12 amino acids, has a length of no more than 50 to 100 amino acids, and/or has a length of between 10 to 100 amino acids. In some embodiments, the peptide described herein may comprise or consist of the peptide of any one of SEQ ID NOs: 1 to 8 or 10 to 16, or a variant thereof that: (a) imparts improved antigen-presentation activity to the steroid acid when conjugated thereto, as compared to the antigen-presentation activity of a corresponding unconjugated steroid acid; (b) has nuclear localization and/or endosomolytic activity; (c) differs from the peptide of any one of SEQ ID NOs: 1 to 8 or 10 to 16 by no more than 1, 2, 3, 4, or 5 amino acid substitutions or deletions; or (d) any combination of (a) to (c).

In some embodiments, the enhancer described herein comprises a steroid acid-peptide conjugate in which the steroid acid is conjugated to the peptide: (a) at a molar ratio of steroid acid: peptide of 1:1, 2:1, 3:1, 4:1, 5:1, 6:1, 7:1, 8:1, 9:1, or 10:1, or between 1:1 to 10:1; (b) at a free amino group and/or a free thiol group (e.g., of a lysine or cysteine) of the peptide; (c) at or towards the N-terminal end of the peptide (e.g., at the free amino group of N terminal residue and/or at the thiol group of an N-terminal cysteine residue); or (d) any combination of (a) to (c). In some embodiments, the steroid acids described herein may be conjugated to the peptide at any suitable functional group within the peptide.

In some embodiments, the molar ratio of enhancer to antigen in a composition as described herein may be at least 0.01:1, 0.05:1, 0.1:1, 0.2:1, 0.5:1, 1:1, 2:1, 3:1, 4:1, 5:1, 6:1, 7:1, 8:1, 9:1, 10:1, 15:1, 20:1; is no more than 2:1, 3:1, 4:1, 5:1, 6:1, 7:1, 8:1, 9:1, 10:1, 15:1, 20:1, 50:1, 100:1, 250:1, 500:1, 1000:1, and/or is between 1:1 to 1000:1; 1:1 to 500:1, 1:1 to 250:1, 1:1 to 200:1.

In some embodiments, antigens described herein may be or may comprise a tumor-associated antigen (TAA), tumor-specific antigen (TSA), a neoantigen, a viral antigen, a bacterial antigen, a fungal antigen, an antigen associated with a disease or disorder amenable to treatment by vaccination and/or immunotherapy; or any antigenic fragment thereof. In some embodiments, antigens described herein may be or may comprise the Spike protein from SARS-CoV-2 or SARS-CoV, or an antigenic variant or antigenic fragment thereof. In some embodiments, the TAA, TSA, and/or neoantigen may be a single-nucleotide variant antigen, a mutational frameshift antigen, splice variant antigen, a gene fusion antigen, an endogenous retroelement antigen, or another class of antigen, such as a human leukocyte antigen (HLA)-somatic mutation-derived antigen or a post-translational TSA (Smith et al., 2019). In some embodiments, the TSA may be a viral-derived cancer antigen, such as from human papillomavirus (HPV), cytomegalovirus, or Epstein-Barr virus (EBV). In some embodiments, the TAA may be or may comprise a cancer-testis antigen, HER2, PSA, TRP-1, TRP-2, EpCAM, GPC3, CEA, MUC1, MAGE-AL NY-ESO-1, SSX-2, mesothelin (MSLN), or EGFR (Patel et al., 2017; Tagliamonte et al., 2014). In some embodiments, antigens described herein may be or may comprise cell lysates or other material derived from a tumor such as tumor-derived exosomes.

In some embodiments, the enhancer as described herein may enable increased cytosolic delivery of the antigen, as compared to a corresponding composition lacking the enhancer. In some embodiments, the enhancer as described herein may enable increased total cellular delivery of the antigen, as compared to a corresponding composition lacking the enhancer. In some embodiments, the enhancer as described herein may enable enhanced cellular immunity against the antigen, as compared to a corresponding composition lacking the enhancer. In some embodiments, the enhancer as described herein may enable increased IFN-gamma production by CD8+ T cells upon exposure to the antigen, as compared to a corresponding composition lacking the enhancer. In some embodiments, the enhancer as described herein may enable enhanced humoral immunity against the antigen, as compared to a corresponding composition lacking the enhancer. In some embodiments, the enhancer as described herein may enable an increased variety (or biodiversity) of antibody species against the antigen, as compared to a corresponding composition lacking the enhancer (e.g., including antibodies against epitopes that are poorly immunogenic).

In some aspects, described herein is a cell culture comprising a population of cells and a composition as described herein (e.g., comprising an antigen and an enhancer of antigen-presentation). In some embodiments, the cells may comprise immune cells (e.g., T cells), antigen-presenting cells (e.g., dendritic cells, macrophages, engineered antigen-presenting cells), MHC class I-expressing cells, MHC class II-expressing cells, or any combination thereof.

In some embodiments, compositions described herein may further comprise a pharmaceutically acceptable excipient and/or adjuvant (e.g., vaccine adjuvant suitable for human or animal use).

In some aspects, described herein is a vaccine comprising a composition as described herein, or comprising cells produced using the cell culture or cell population as described herein. In some embodiments, the vaccine may be a therapeutic or prophylactic vaccine (e.g., anti-cancer vaccine, anti-viral vaccine, or anti-bacterial vaccine). In some embodiments, the immunogen enhancers described herein may enable a decrease in the quantity of antigen and/or antigen-presenting cells formulated in an immunogenic composition (e.g., vaccine) required to generate an immune response, as compared to in the absence of the immunogen enhancer.

In some aspects, described herein is a method for triggering an enhanced adaptive immune response in a subject against an antigen of interest, the method comprising administering to the subject a composition as described herein, or cells produced using the cell culture as described herein.

In some aspects, described herein is a method for vaccinating a subject against an infectious disease, the method comprising administering to the subject a composition as described herein, or cells produced using a cell culture as described herein, wherein the antigen comprises an antigenic fragment of a pathogen (e.g., virus, bacteria, fungus) causing the infectious disease.

In some aspects, described herein is a method for treating cancer in a subject, the method comprising administering to the subject a composition as described herein, or cells produced using a cell culture as described herein, wherein the antigen is overexpressed or aberrantly expressed in cells causing the cancer.

In a further aspect, described herein is a method for treating or preventing a disease or disorder amenable to treatment by vaccination and/or immunotherapy, the method comprising administering an immunogenic composition as described herein to the subject.

In some aspects, described herein is a steroid acid-peptide conjugate for use in admixture with an antigen. In some embodiments, the admixture of the steroid acid-peptide conjugate with the antigen enables: (i) increased cytosolic delivery of the antigen, as compared to a corresponding composition lacking the enhancer; (ii) increased total cellular delivery of the antigen, as compared to a corresponding composition lacking the enhancer; (iii) enhanced cellular immunity against the antigen, as compared to a corresponding composition lacking the enhancer; (iv) increased IFN-gamma production by CD8+ T cells upon exposure to the antigen, as compared to a corresponding composition lacking the enhancer; (v) enhanced humoral immunity against the antigen, as compared to a corresponding composition lacking the enhancer; (vi) an increased variety of antibody species against the antigen, as compared to a corresponding composition lacking the enhancer; or (vii) any combination of (i) to (vi).

In some aspects, described herein is a composition as described herein, or the cell population produced using a culture as described herein, for use in therapy.

In some aspects, described herein is the use of a composition as described herein, or the cell population produced using a culture as described herein, for generating an immune response in a subject or for the manufacture of a medicament (e.g., vaccine) for generating an immune response in a subject. In some embodiments, the immune response may comprise enhanced cellular immunity against the antigen, increased IFN-gamma production by CD8+ T cells upon exposure to said antigen, enhanced humoral immunity against said, or any combination thereof, as compared to that generated from a corresponding composition or cell culture lacking the enhancer.

Items

In some aspects, described herein are one or more of the following items:

1. A composition comprising an antigen admixed with an enhancer of antigen-presentation, the enhancer comprising a steroid acid and/or a steroid acid-peptide conjugate in an amount sufficient to improve presentation of the antigen upon administration of the composition to antigen-presenting cells, as compared to administration of a corresponding composition lacking the enhancer.
2. The composition of item 1, wherein the steroid acid in the enhancer or in the steroid acid-peptide conjugate, is a steroid acid that triggers ceramide accumulation on the inner leaflet of endosomes, thereby destabilizing endosomal membranes within the antigen-presenting cells and facilitating endosomal escape of the antigen to the cytosol.
3. The composition of item 1 or 2, wherein the steroid acid in the enhancer or in the steroid acid-peptide conjugate, is a steroid acid that triggers increased acid sphingomyelinase (ASM)-mediated cleavage of sphingomyelin to form ceramide.
4. The composition of any one of items 1 to 3, wherein the steroid acid in the enhancer or in the steroid acid-peptide conjugate, is a bile acid.
5. The composition of any one of items 1 to 4, wherein the steroid acid in the enhancer or in the steroid acid-peptide conjugate, is a primary bile acid or a secondary bile acid.
6. The composition of any one of items 1 to 5, wherein the steroid acid in the enhancer or in the steroid acid-peptide conjugate, is or comprises: (a) a bile acid which is: cholic acid (CA), chenodeoxycholic acid (CDCA), deoxycholic acid (DCA), lithocholic acid (LCA), glycocholic acid (GCA), taurocholic acid (TCA), glycodeoxycholic acid (GDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA); (b) an analog of the bile acid of (a) that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid; (c) a bile acid or bile acid analog that is more hydrophobic than cholic acid (e.g., CDCA, DCA, LCA, TCA, TDCA, TCDCA, GCA, GDCA, or GCDCA); or (d) any combination of (a) to (c).

7. The composition of any one of items 1 to 6, wherein the steroid acid in the enhancer or in the steroid acid-peptide conjugate, is or comprises: glycodeoxycholic acid (GDCA), glycochenodeoxycholic acid (GCDCA), ursodeoxycholic acid (UDCA), or lithocholic acid (LCA).

8. The composition of any one of items 1 to 7, wherein the peptide comprises a nuclear localization signal (NLS).

9. The composition of item 8, wherein the NLS is a classical NLS (e.g., comprising a K-K/R-X-K/R motif), a PY-NLS (e.g., comprising one or more PY motifs, such as towards the C-terminal end of the NLS, or comprising the motif R-$X_{2-5}$-PY and/or having Kapβ2-binding activity), a PL-NLS (e.g., comprising one or more PL motifs, such as towards the C-terminal end of the NLS), a ribosomal NLS, an NLS further comprising a nucleolar targeting signal, or any combination thereof 10. The composition of item 8 or 9, wherein the NLS is or is from an SV40 NLS, a cMyc NLS, an hnRNPA1 M9 NLS, an hnRNP D NLS, an hnRNP M NLS, a PQBP-1 NLS, an HuR NLS, Tus NLS, nucleoplasmin NLS, NLS1 RPS17, NLS2 RPS17, NLS3 RPS17, or NLS2-RG domain RSP17.

11. The composition of any one of items 8 to 10, wherein the NLS comprises at least three acidic residues (e.g., R/K) and/or at least three basic residues (e.g., E/D).

12. The composition of any one of items 1 to 11, wherein the peptide comprises an endosomolytic motif that facilitates endosomal escape.

13. The composition of any one of items 1 to 12, wherein the peptide comprises a protein transduction domain that stimulates endocytosis and/or endosomal formation.

14. The composition of any one of items 1 to 12, wherein the peptide lacks a protein transduction domain or cell penetrating peptide.

15. The composition of any one of items 1 to 14, wherein the peptide is a non-immunogenic peptide.

16. The composition of any one of items 1 to 15, wherein the peptide has a length of at least 7, 8, 9, 10, 11, or 12 amino acids, has a length of no more than 50 to 100 amino acids, and/or has a length of between 10 to 100 amino acids.

17. The composition of any one of items 1 to 16, wherein the peptide comprises or consists of the peptide of any one of SEQ ID NOs: 1 to 8 or 10 to 16, or a variant thereof that: (a) imparts improved antigen-presentation activity to the steroid acid when conjugated thereto, as compared to the antigen-presentation activity of a corresponding unconjugated steroid acid; (b) has nuclear localization and/or endosomolytic activity; (c) differs from the peptide of any one of SEQ ID NOs: 1 to 8 or 10 to 16 by no more than 1, 2, 3, 4, or 5 amino acid substitutions or deletions; or (d) any combination of (a) to (c).

18. The composition of any one of items 1 to 17, wherein the enhancer comprises a steroid acid-peptide conjugate in which the steroid acid is conjugated to the peptide: (a) at a molar ratio of steroid acid: peptide of 1:1, 2:1, 3:1, 4:1, 5:1, 6:1, 7:1, 8:1, 9:1, or 10:1; or between 1:1 to 10:1; (b) at a free amino group and/or a free thiol group (e.g., of a lysine or cysteine) of the peptide; (c) at or towards the N-terminal end of the peptide (e.g., at the free amino group of N terminal residue and/or at the thiol group of an N-terminal cysteine residue); or (d) any combination of (a) to (c).

19. The composition of any one of items 1 to 18, wherein the molar ratio of enhancer to antigen in the composition is at least 0.01:1, 0.05:1, 0.1:1, 0.2:1, 0.5:1, 1:1, 2:1, 3:1, 4:1, 5:1, 6:1, 7:1, 8:1, 9:1, 10:1, 15:1, 20:1; is no more than 2:1, 3:1, 4:1, 5:1, 6:1, 7:1, 8:1, 9:1, 10:1, 15:1, 20:1, 50:1, 100:1, 250:1, 500:1, 1000:1, and/or is between 1:1 to 1000:1; 1:1 to 500:1, 1:1 to 250:1, 1:1 to 200:1.

20. The composition of any one of items 1 to 19, wherein the antigen is a polypeptide antigen comprising one or more MHC class I epitopes and/or MHC class II epitopes.

21. The composition of item 20, wherein the polypeptide antigen is or comprises: (a) a tumor-associated antigen (TAA), tumor-specific antigen (TSA), a neoantigen, a viral antigen, a bacterial antigen, a fungal antigen, an antigen associated with a disease or disorder amenable to treatment by vaccination and/or immunotherapy; or any antigenic fragment thereof; or (b) a corona viral antigen (e.g., SARS-CoV-2 Spike protein, SARS-CoV Spike protein, or an antigenic fragment thereof; or a cancer antigen, such as a single-nucleotide variant antigen, a mutational frameshift antigen, splice variant antigen, a gene fusion antigen, an endogenous retroelement antigen, or another class of antigen, such as a human leukocyte antigen (HLA)-somatic mutation-derived antigen or a post-translational TSA, a viral-derived cancer antigen (e.g., from human papillomavirus (HPV), cytomegalovirus, or Epstein-Barr virus (EBV)), a cancer-testis antigen, HER2, PSA, TRP-1, TRP-2, EpCAM, GPC3, CEA, MUC1, MAGE-A1, NY-ESO-1, SSX-2, mesothelin (MSLN), EGFR, cell lysates or other material derived from a tumor (e.g., tumor-derived exosomes).

22. The composition of any one of items 1 to 21, wherein the enhancer enables: (i) increased cytosolic delivery of the antigen, as compared to a corresponding composition lacking the enhancer; (ii) increased total cellular delivery of the antigen, as compared to a corresponding composition lacking the enhancer; (iii) enhanced cellular immunity against the antigen, as compared to a corresponding composition lacking the enhancer; (iv) increased IFN-gamma production by CD8+ T cells upon exposure to the antigen, as compared to a corresponding composition lacking the enhancer; (v) enhanced humoral immunity against the antigen, as compared to a corresponding composition lacking the enhancer; (vi) an increased variety of antibody species against the antigen, as compared to a corresponding composition lacking the enhancer; or (vii) any combination of (i) to (vi).

23. The composition of any one of items 1 to 22, further comprising a pharmaceutically acceptable excipient and/or adjuvant.

24. A cell culture comprising a population of cells and the composition as defined in any one of items 1 to 23.

25. The cell culture of item 24, wherein the cells comprise immune cells (e.g., T cells), antigen-presenting cells (e.g., dendritic cells, macrophages, engineered antigen-presenting cells), MHC class I-expressing cells, MHC class II-expressing cells, or any combination thereof 26. A vaccine comprising the composition as defined in any one of items 1 to 22, or comprising cells produced using the cell culture as defined in item 24 or 25.

27. The vaccine of item 26, which is a therapeutic or prophylactic vaccine (e.g., anti-cancer vaccine, anti-viral vaccine, or anti-bacterial vaccine).

28. A method for triggering an enhanced adaptive immune response in a subject against an antigen of interest, the method comprising administering to the subject the composition as defined in any one of items 1 to 23, or cells produced using the cell culture as defined in item 24 or 25.
29. A method for vaccinating a subject against an infectious disease, the method comprising administering to the subject the composition as defined in any one of items 1 to 23 or cells produced using the cell culture as defined in item 24 or 25, wherein the antigen comprises an antigenic fragment of a pathogen (e.g., virus, bacteria, fungus) causing the infectious disease.
30. A method for treating cancer in a subject, the method comprising administering to the subject the composition as defined in any one of items 1 to 23 or cells produced using the cell culture as defined in item 24 or 25, wherein the antigen is a overexpressed or aberrantly expressed in cells causing the cancer.
31. A steroid acid-peptide conjugate for use in admixture with an antigen.
32. The steroid acid-peptide conjugate for use of item 31, wherein the steroid acid-conjugate and/or the antigen is/are as defined in any one of items 1 to 22.
33. Use of the composition as defined in any one of items 1 to 23, or the cell culture as defined in item 24 or 25, for generating an immune response in a subject or for the manufacture of a medicament (e.g., vaccine) for generating an immune response in a subject.
34. The use of item 33, wherein the immune response comprises enhanced cellular immunity against said antigen, increased IFN-gamma production by CD8+ T cells upon exposure to said antigen, enhanced humoral immunity against said, or any combination thereof, as compared to that generated from a corresponding composition or cell culture lacking the enhancer.

EXAMPLES

Example 1: General Materials and Methods

Generation of the Bile Acid-NLS Moieties

Bile acid-NLS moieties were synthesized similar to the synthesis of cholic acid-NLS (ChAcNLS) as previously described in Beaudoin et al., 2016. For example, for CA-SV40NLS, cholic acid was conjugated to the free amino group of the N-terminal cysteine residue of a 13-mer peptide (CGYGPKKKRKVGG; SEQ ID NO: 1) that comprises a nuclear localization signal from SV40 large T-antigen (SEQ ID NO: 2) flanked by linker amino acids.

Generation of Bone Marrow Derived Dendritic Cells

Mouse bone marrow derived dendritic cells (BMDCs) were generated by flushing the whole marrow from mouse femurs using RPMI™ 1640 supplemented with 10% fetal bovine serum (FBS), 50 U/mL Penicillin-Streptomycin, 2 mM L-glutamine, 10 mM HEPES, 1% MEM Non-essential Amino Acids, 1 mM Sodium Pyruvate, 0.5 mM beta-mercaptoethanol. Following red blood cell lysis, cells were then cultured in media supplemented with 50 ng/mL murine recombinant GM-CSF. The media was changed on days 2, 4, 6 and 8. On day 9, the media was replaced to include recombinant murine GM-CSF and LPS from *Escherichia coli* O111 (1 ng/mL) to stimulate dendritic cell (DC) maturation. Mature DCs were assessed by flow cytometry for their surface expression of CD3, CD19, NK1.1, CD11c, CD80, CD86, and I-Ab.

Antigen Cross-Presentation Assay

To evaluate antigen cross-presentation, cells were seeded at $25 \times 10^3$ cells per well in 24-well plates (Corning; Massachusetts, United States), then pulsed with antigens or antigen-containing mixtures at different concentrations for 3 h. At the end of the pulsing period, the cells were washed to remove excess antigen and co-cultured with $10^6$/mL CD8 T-cells purified from the spleens of OT-I mice using T-cell isolation kits according to the manufacturer's protocol. After 72 hours, supernatants were collected and used to quantify cytokine production by commercial enzyme-linked immunosorbent assays (ELISAs).

Antigen-Presentation Assay Using the B3Z Reporter System

Various bile acid-NLS conjugates were screened using the B3Z reporter system. The B3Z cell line is a T-cell hybridoma specific for the H2-K$^b$-SIINFEKL complex. Once activated via its TCR, the LacZ reporter gene (under the NFAT promoter control) is expressed. Briefly, $1.5 \times 10^5$ BMDCs or $2.5 \times 10^5$ MSCs were co-cultured with $5 \times 10^4$ B3Z cells treated with the mixing conditions of ovalbumin (OVA) and bile acid-NLS conjugates for overnight at 37° C. with 5% $CO_2$. The following day, all cells were washed twice with PBS (pH 7.4), and the cell pellets were lysed by adding 100 μL of a lysis buffer containing 0.15 mM chlorophenol red-beta-D-galactopyranoside (CPRG) substrate (Calbiochem, La Jolla, Calif.), 0.125% NP40 (EMD Sciences, La Jolla, Calif.), 9 mM $MgCl_2$ (Aldrich, USA) and 100 mM 2-mercaptoethanol in PBS. After a 5- or 24-h incubation at 37° C., absorbance was taken at 570 nm with 636 nm as the reference wavelength. For these experiments, OVA was re-suspended in PBS (pH 7.3) at 5-10 mg/mL. The different bile acid-NLS conjugates were re-suspended in $H_2O$ at 10 mg/mL. Bile acid-NLS conjugate: antigen mixtures were prepared at different molar ratios according to Table 2.

TABLE 2

| Molar Ratios of Bile Acid-NLS conjugate:OVA | | | | | |
|---|---|---|---|---|---|
| Molar ratio (bile acid-NLS conjugate: OVA) | 2.2:1 (50 μmol/L) | 4:1 | 8:1 | 12:1 | 22:1 (500 μmol/L) |
| OVA (mmol) | $2.27273 \times 10^{-5}$ (1 mg) | $2.27273 \times 10^{-5}$ (1 mg) | $2.27273 \times 10^{-5}$ (1 mg) | $2.27273 \times 10^{-5}$ (1 mg) | $2.27273 \times 10^{-5}$ (1 mg) |
| Bile acid-NLS conjugate (mmol) | 0.00005 | $9.09091 \times 10^{-5}$ | 0.00018182 | 0.000272727 | 0.0005 |

Example 2: Cholic Acid and Cholic Acid-SV40NLS Enhance Cross Presentation/Immunogenicity of OVA Antigen Cross presentation assays were performed to screen for agents that could improve the cross-presentation and/or immunogenicity of antigens upon non-covalent mixture therewith. Mouse BMDCs were pre-pulsed with either antigen alone, or antigens mixed with candidate immunogen enhancers at different ratios. The pulsed BMDCs were then co-cultured with CD8 T-cells derived from the spleens of OT-I mice and the amount of IFN-gamma produced by the CD8 T-cells was quantified as a measure of cross presentation activity. Preliminary screens identified cholic acid and cholic acid-NLS peptide conjugates as potential immunogen enhancers. FIG. 1 shows the results of cross presentation assays in which BMDCs were pre-pulsed with the antigen ovalbumin alone ("OVA alone"), cholic acid alone ("CA alone"), a cholic acid-NLS peptide conjugate alone ("CA-SV40NLS alone"), or different ratios of cholic acid:antigen mixtures ("CA:OVA") or cholic acid-NLS peptide conjugate:antigen mixtures ("CA-SV40NLS:OVA"). Interestingly, BMDCs pre-pulsed with the highest ratios of cholic acid: antigen mixtures (CA:OVA) tested resulted in an increased by up to 3-fold of the amount of IFN-gamma produced, as compared to BMDCs pre-pulsed with the OVA antigen alone. Strikingly, BMDCs pre-pulsed with the highest ratios of cholic acid-NLS peptide conjugate:antigen mixtures (CA-SV40NLS:OVA) tested resulted in a 6- to 7-fold increase in the amount of IFN-gamma produced, as compared to BMDCs pre-pulsed with the OVA antigen alone.

Figure 2:
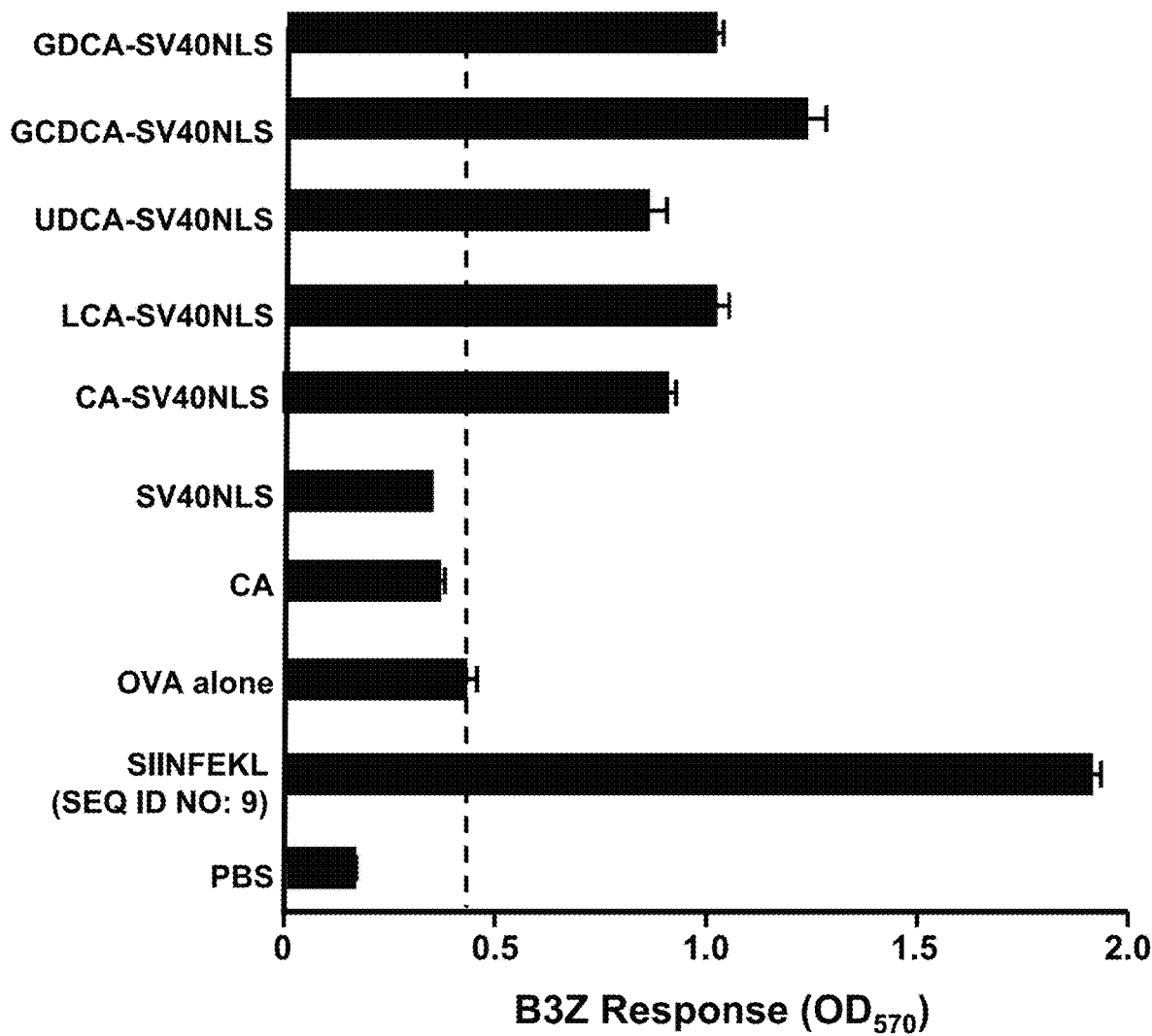
FIG. 2 shows the effect of different bile acids on the antigen presentation activity of bile acid-SV40NLS conjugates. For this experiment, BMDCs were used as the antigen presenting cells (n=6) and the molar ratio (bile acid/peptide/conjugate): antigen was 4:1. Controls tested included no antigen ("PBS"), antigen alone ("OVA alone"), unconjugated NLS peptide ("SV40NLS"), unconjugated cholic acid mixed with OVA ("CA"), and the positive control peptide SIINFEKL (SEQ ID NO: 9) mixed with OVA ("SIINFEKL"). The dashed line represents the signal obtained with OVA alone. Bile acids: cholic acid (CA); glycodeoxycholic acid (GDCA); glycochenodeoxycholic acid (GCDCA); ursodeoxycholic acid (UDCA); and lithocholic acid (LCA).

Example 3: Enhanced Antigen Presentation in the Presence of SV40NLS Conjugated to Different Bile Acids Variants of CA-SV40NLS were synthesized in order to explore structure-activity relationships relating to the antigen cross-presentation enhancing activity observed for this conjugate. More particularly, conjugates having different bile acids conjugated to the SV40NLS peptide (SEQ ID NO: 1) were synthesized and their effect on antigen presentation was evaluated by using the B3Z reporter system with the OVA antigen as described in Example 1. The results in FIG. 2 show that increased antigen cross-presentation was observed when OVA was mixed with the CA-SV40NLS conjugate as compared to the OVA antigen alone ("OVA alone"; dashed line). These results were consistent with those observed using the OT-I CD8 T cell-based assay (FIG. 1). Interestingly, comparable or higher antigen cross-presentation to CA-SV40NLS was observed when cholic acid was replaced with the bile acids: glycodeoxycholic acid (GDCA), glycochenodeoxycholic acid (GCDCA), ursodeoxycholic acid (UDCA), or lithocholic acid (LCA). In FIG. 2, no increase in antigen cross-presentation over the antigen alone ("OVA") was observed when OVA was mixed with either unconjugated cholic acid ("CA") or SV40NLS peptide ("SV40NLS"), although lower sensitivity of the B3Z reporter system as compared to the OT-I CD8 T cell-based assay used in FIG. 1 may have been a factor. Interestingly, subsequent assays using the same B3Z reporter system revealed up to about a 30% increase in B3Z response ($OD_{570}$) when OVA was mixed with unconjugated glycoursodeoxycholic acid (GUDCA; 22:1) over the OVA alone (data not shown). Furthermore, the immunogen enhancer activity of GUDCA was observed at all GUDCA:OVA molar ratios tested (i.e., 2:1, 4:1, 8:1, 12:1 and 22:1).

Example 4: Enhanced Antigen Presentation in the Presence of SV40NLS Conjugated to Different Bile Acids Further variants of CA-SV40NLS were synthesized in which the SV40NLS peptide was replaced with peptides comprising other NLS's (Table 3) and the antigen presentation activities of the CA-NLS peptide conjugates were evaluated using the B3Z reporter system as described in Example 1. The following conjugate:antigen molar ratios were tested for each conjugate: 2:1, 4:1, 8:1, 12:1 and 22:1. The results in FIGS. 3-6 compare the antigen presentation activities of different conjugates at the conjugate:antigen ratio that yielded the highest B3Z response (OD570) for that conjugate.

TABLE 3

NLS peptides characterized in FIGS. 3-8D

| NLS type | Peptide name | Peptide sequence | SEQ ID NO: |
|---|---|---|---|
| Classical NLS (K-K/R-X-K/R) | SV40NLS | CGYGPKKKRKVGG | 1 |
| | GWG-SV40NLS | CGWWGYGPKKKR KVGGWWG | 3 |
| | hnRNPA1 M9 NLS | CSNFGPMKGGN FGGRSSGPY | 4 |
| | hnRNPDNLS | CSGYGKVSRRG GHQNSYKPY | 5 |
| | PQBP-1 NLS | CADREEGKERRH HRREELAPY | 6 |
| PY/G-NLS (hydrophobic & basic) | hnRNPMNLS | CNEKRKEKNIKR GGNRFEPY | 10 |
| | cMyc NLS | CGYGPAAKRVKLDGG | 12 |
| | HuR NLS | CGRFSPMGVDHMS GLSGVNVPG | 13 |
| | Tus NLS | CGYGKLKIKRPVKGG CNKRVCEEIAIIPS KKLRNK | 14 |
| | NLS2-RG Domain RRPS17 | GSGRIQRGPVRGIS | 11 |
| | NLS1RPS17 | CMGRVRTKTVKK AAGG | 15 |
| Ribosomal NLS | NLS2 RPS17 | CNKRVCEEIAII PSKKLRNK | 7 |
| | NLS3 RPS17 | SKKLRNKIAGYVTH LMKRI | 8 |

The results in FIGS. 3-6 generally show that increased antigen presentation can be achieved by exposing antigen-presenting cells to the antigen in the presence of cholic acid conjugated to peptides comprising nuclear localisation signals of different types and having different amino acid sequences.

Figure 3:
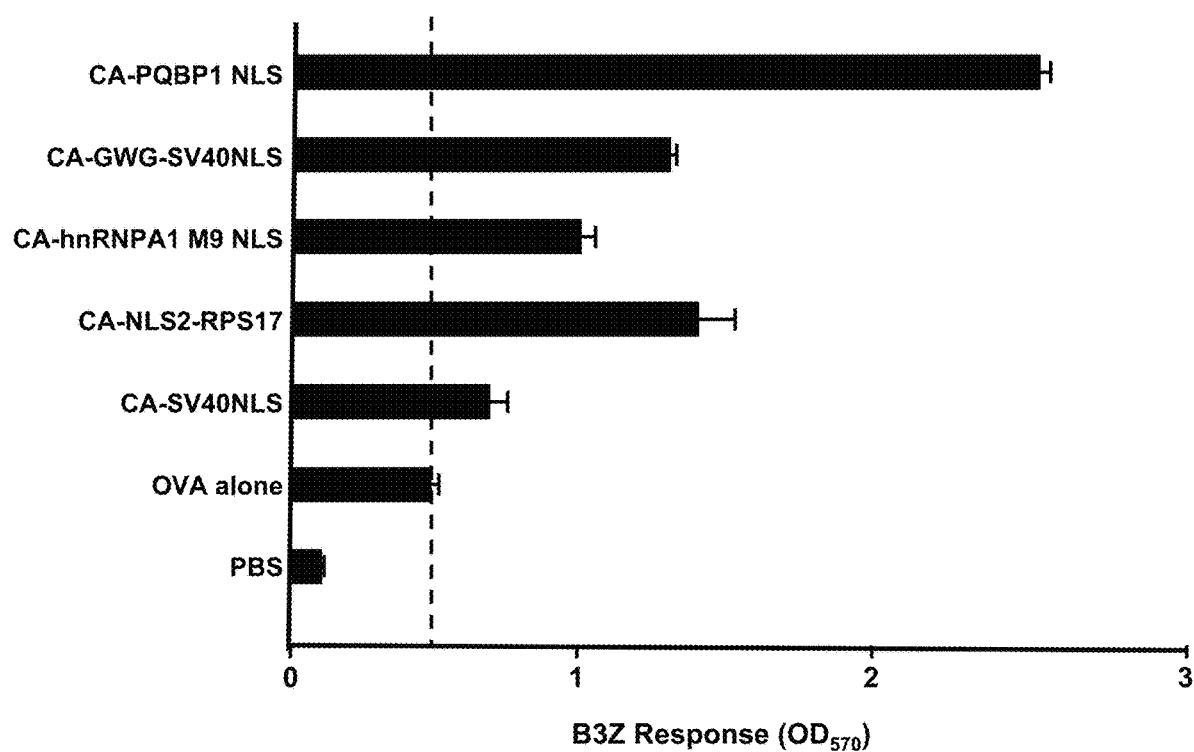
FIG. 3 shows the effect of different NLS peptides on the antigen presentation activity of cholic acid-NLS peptide conjugates. The dashed line represents the signal obtained with OVA alone. The readout was taken after 24 h of incubation and error bars represent SD (n=6). For this experiment, BMDCs were used as the antigen presenting cells.
Figure 4:
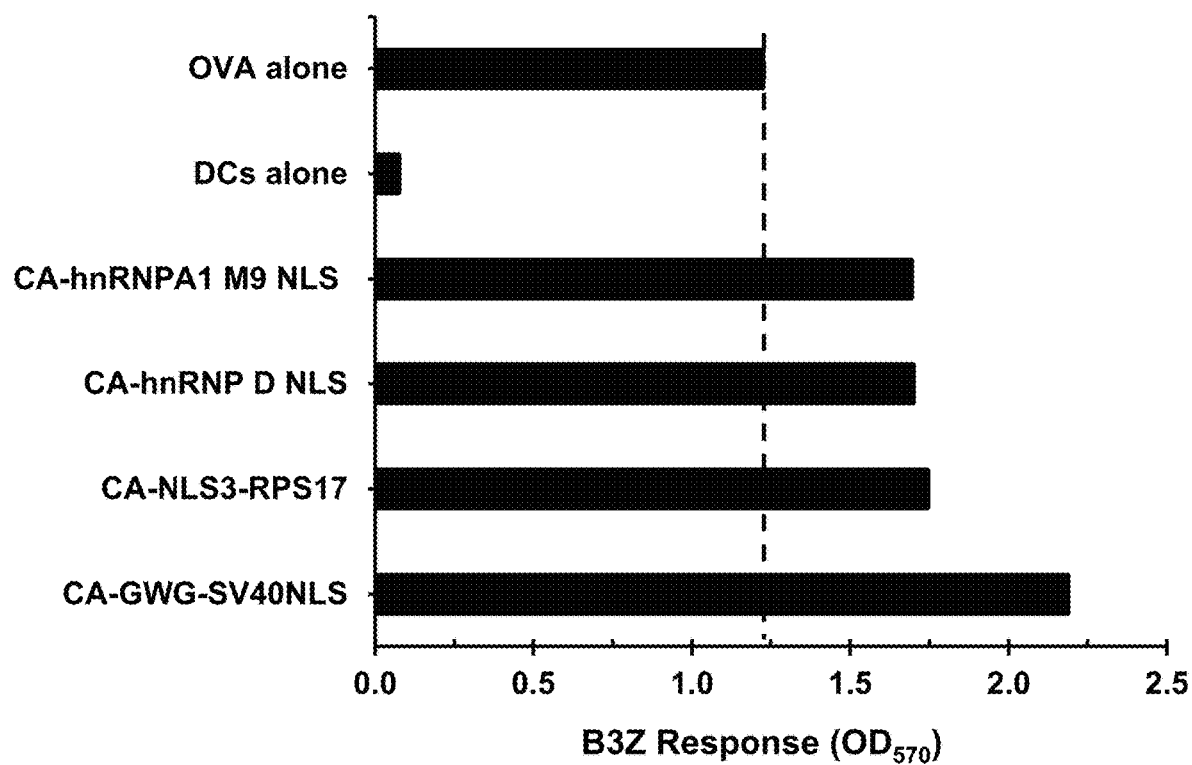
FIG. 4 shows the effect of different NLS peptides on the antigen presentation activity of cholic acid-NLS peptide conjugates. The dashed line represents the signal obtained with OVA alone. Readout was taken after 24 h of incubation from a single experiment. The molar ratio of CA-peptide conjugate: OVA was 22:1. For this experiment, BMDCs were used as the antigen presenting cells.
Figure 5:
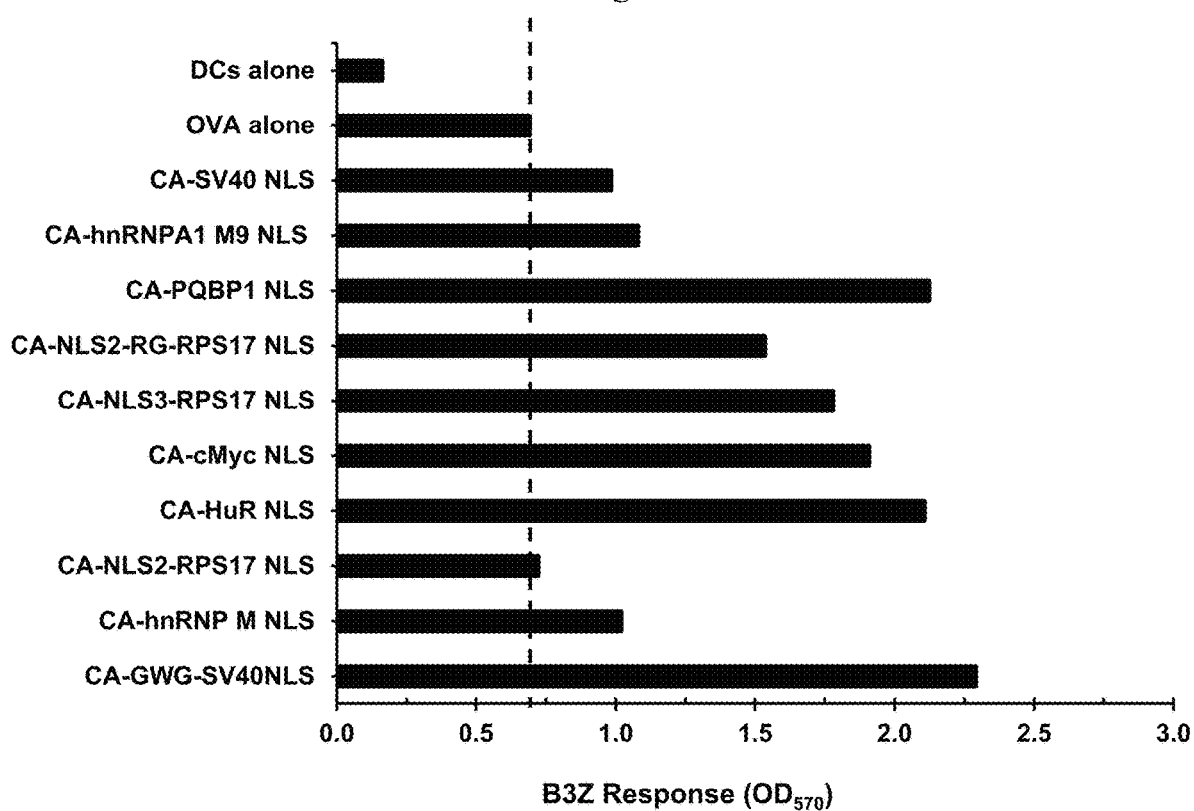
FIG. 5 shows the effect of different NLS peptides on the antigen presentation activity of cholic acid-NLS peptide conjugates. For this experiment, BMDCs were used as the antigen presenting cells. The dashed line represents the signal obtained with OVA alone. Readout was taken after 24 h of incubation from a single experiment. The molar ratio of CA-peptide conjugate: OVA was as follows: CA-GWG-SV40NLS (12:1); CA-hnRNP M NLS (12:1); CA-NLS2-RPS17 NLS (22:1); CA-HuR NLS (22:1); CA-cMyc NLS (2:1); CA-NLS3-RPS17 NLS (22:1); CA-NLS2-RG-RPS17 NLS (2:1); CA-PQBP1 NLS (8:1); CA-hnRNPA1 M9 NLS (22:1); and CA-SV40 NLS (2:1).

Using BMDCs as antigen presenting cells, the glutamate-rich peptide PQBP-1 NLS was associated with strikingly high antigen-presentation activity (FIGS. 3 and 5). Furthermore, NLS2-RG Domain RPS17, NLS3-RPS17, cMyc NLS, and HuR NLS peptides were also associated with high antigen presentation activity. Interestingly, the peptide GWG-SV40NLS was associated with higher antigen-presentation activity than SV40NLS, suggesting that the addition of flanking aromatic amino acids (WW or GWWG) was beneficial for activity (see FIGS. 3-5). Similar results were observed using a DC cell line (DC2.4) as antigen presenting cells.

Figure 6:
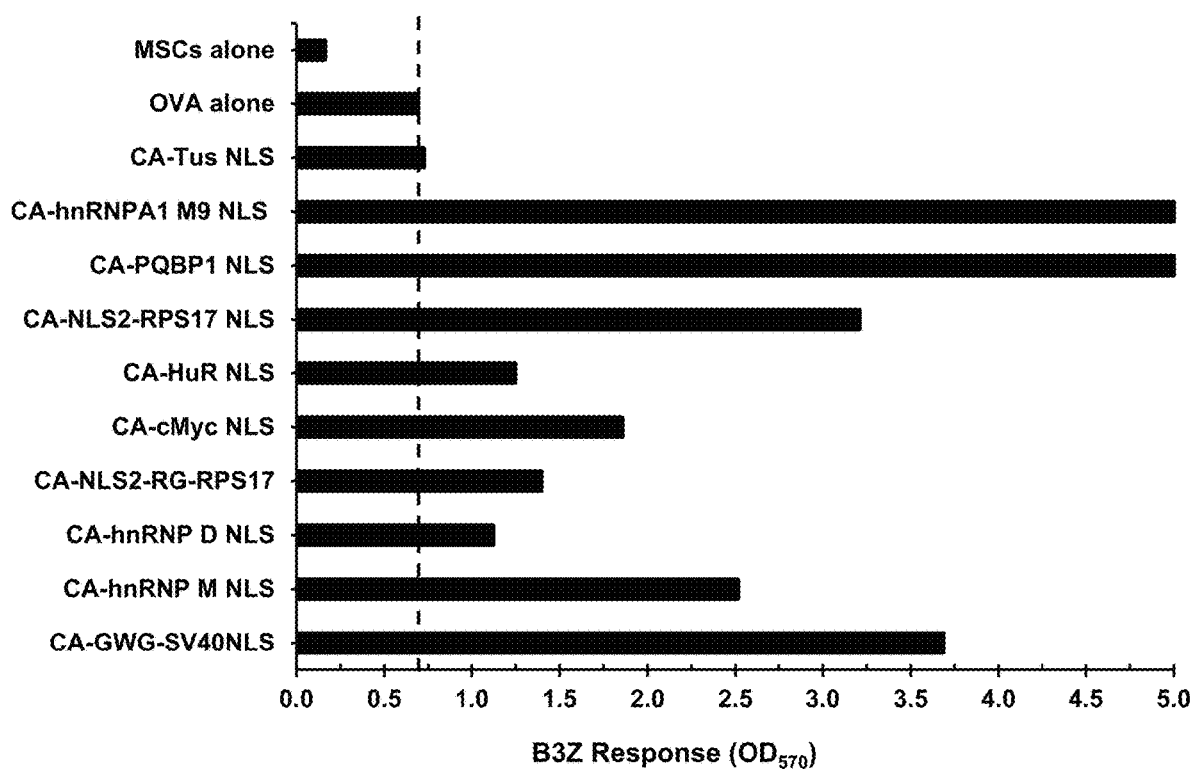
FIG. 6 shows the effect of different NLS peptides on the antigen presentation activity of cholic acid-NLS peptide conjugates. For this experiment, a cross-presentation mesenchymal stromal cell (MSC) line was used as the antigen presenting cells. The dashed line represents the signal obtained with OVA alone. Readout was taken after 24 h of incubation. The molar ratio of CA-peptide conjugate: OVA was as follows: CA-GWG-SV40NLS (2:1); CA-hnRNP M NLS (8:1); CA-hnRNP D NLS (12:1); CA-NLS2-RG-RPS17 (4:1); CA-cMyc NLS (12:1); CA-HuR NLS (12:1); CA-Tus NLS (2:1); CA-NLS2-RPS17 NLS (4:1); CA-PQBP1 NLS (12:1); CA-hnRNPA1 M9 NLS (2:1); and CA-SV40 NLS (2:1).
Figure 7A:
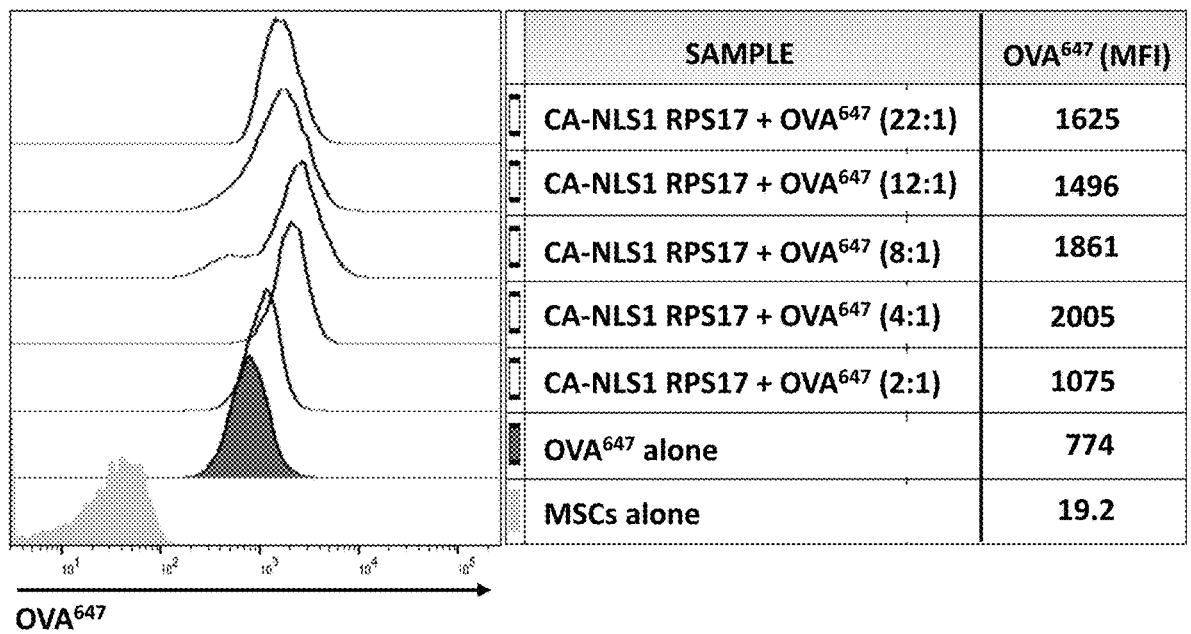
FIGS. 7A to 7D show the effect of different NLS peptides on the antigen internalization activity of cholic acid-NLS peptide conjugates. For this experiment, a cross-presenting mesenchymal stromal cell (MSC) line was used as the antigen presenting cells, which were pulsed with OVA labelled with Alexa Fluor 647 (i.e., OVA$^{647}$)™. OVA$^{647}$ fluorescence was measured by flow cytometry. Different ratios of CA (NLS1 RPS17 [FIG. 7A]; NLS3 RPS17 [FIG. 7B]; PQBP-1 [FIG. 7C]; and hnRNPA1 M9 NLS [FIG. 7D]) to antigen (CA:OVA=22:1, 12:1, 8:1, 4:1, and 2:1) were tested (hnRNPA1 M9 NLS at 2:1).
Figure 7B:
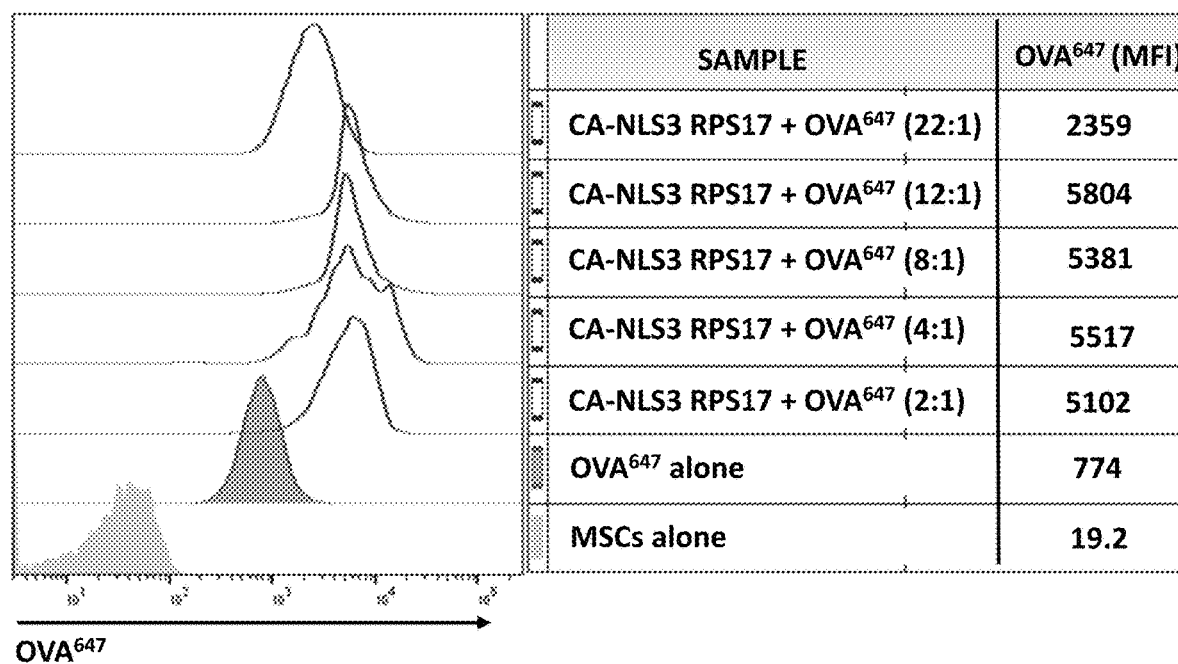
Figure 7C:
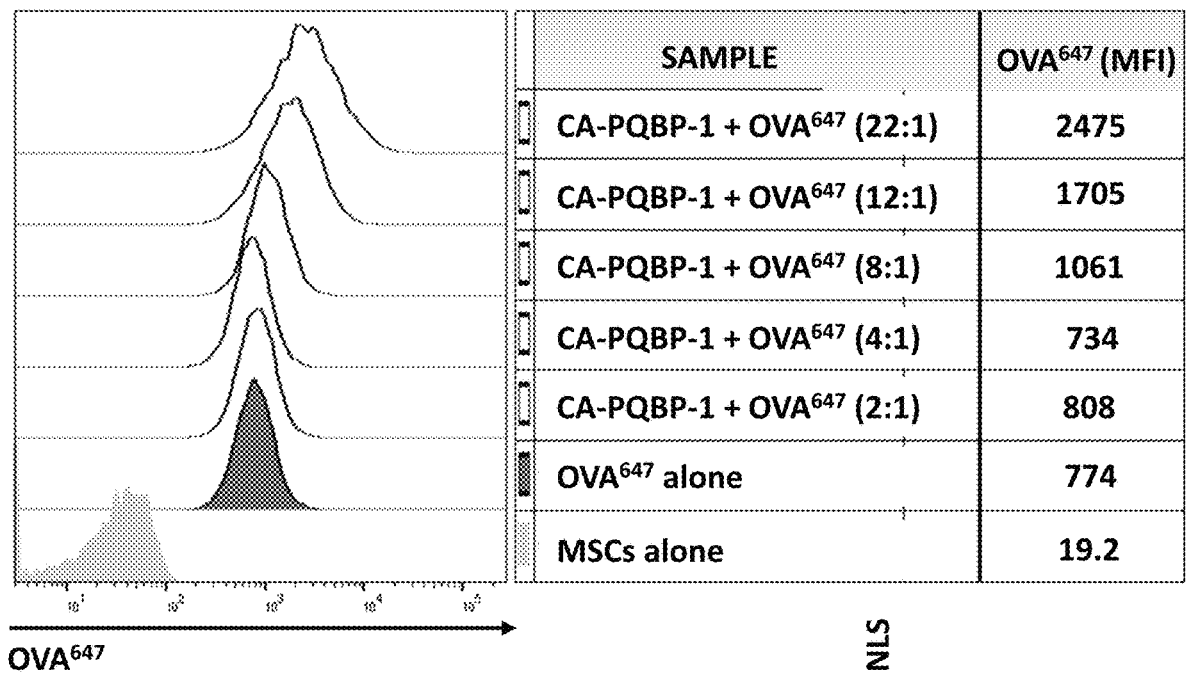
Figure 7D:
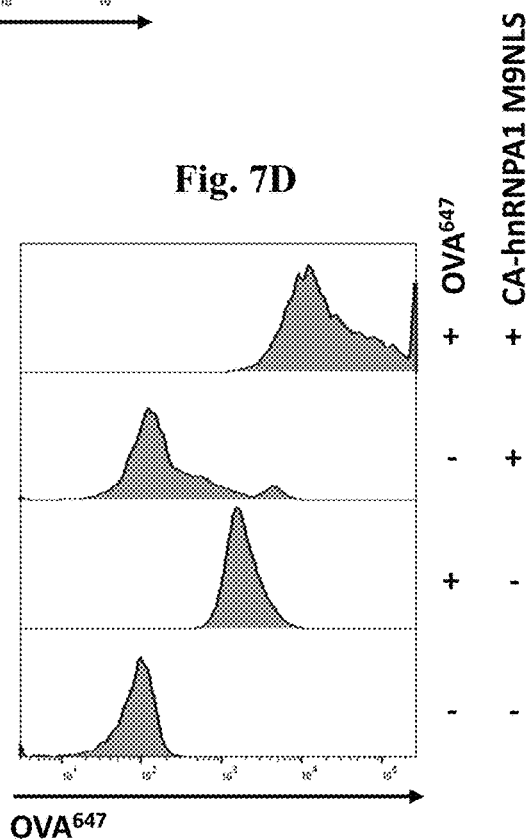
Figure 8A:
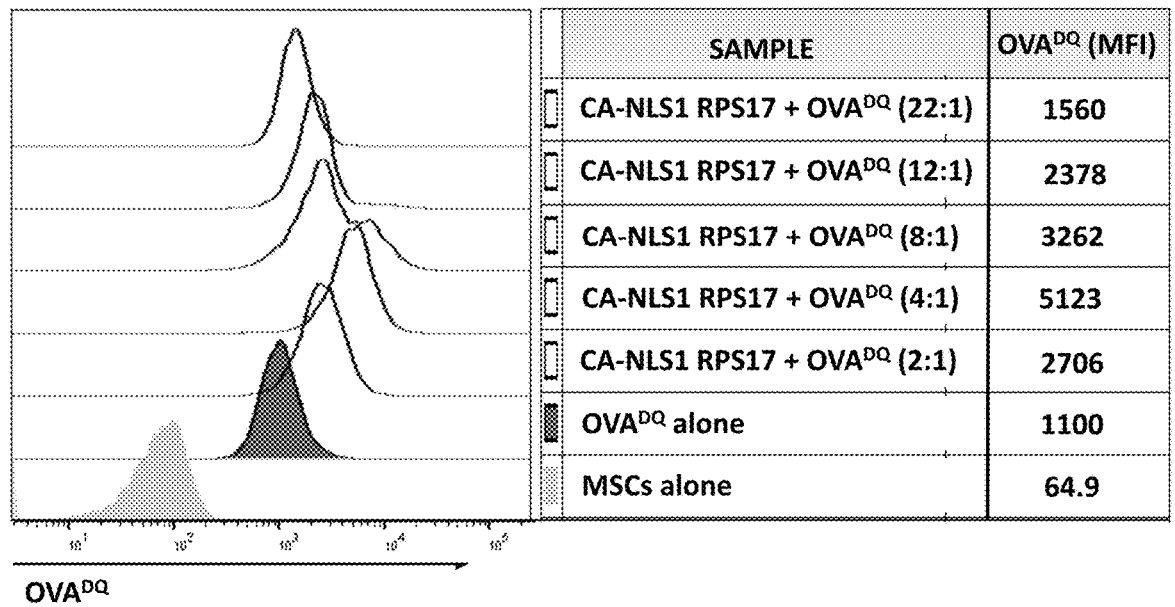
FIGS. 8A to 8D show the effect of different NLS peptides on the antigen processing activity of cholic acid-NLS peptide conjugates. For this experiment, a cross-presenting mesenchymal stromal cell (MSC) line was used as the antigen presenting cells, which were pulsed with DQ™ Ovalbumin (i.e., OVA$^{DQ}$). OVA$^{DQ}$ fluorescence was measured by flow cytometry. Different ratios of CA (NLS1 RSP17 [FIG. 8A]; NLS3 RPS17 [FIG. 8B]; PQBP-1 [FIG. 8C]; and hnRNPA1 M9 NLS [FIG. 8D]) to antigen (CA:OVA=22:1, 12:1, 8:1, 4:1, and 2:1) were tested (hnRNPA1 M9 NLS at 2:1).
Figure 8B:
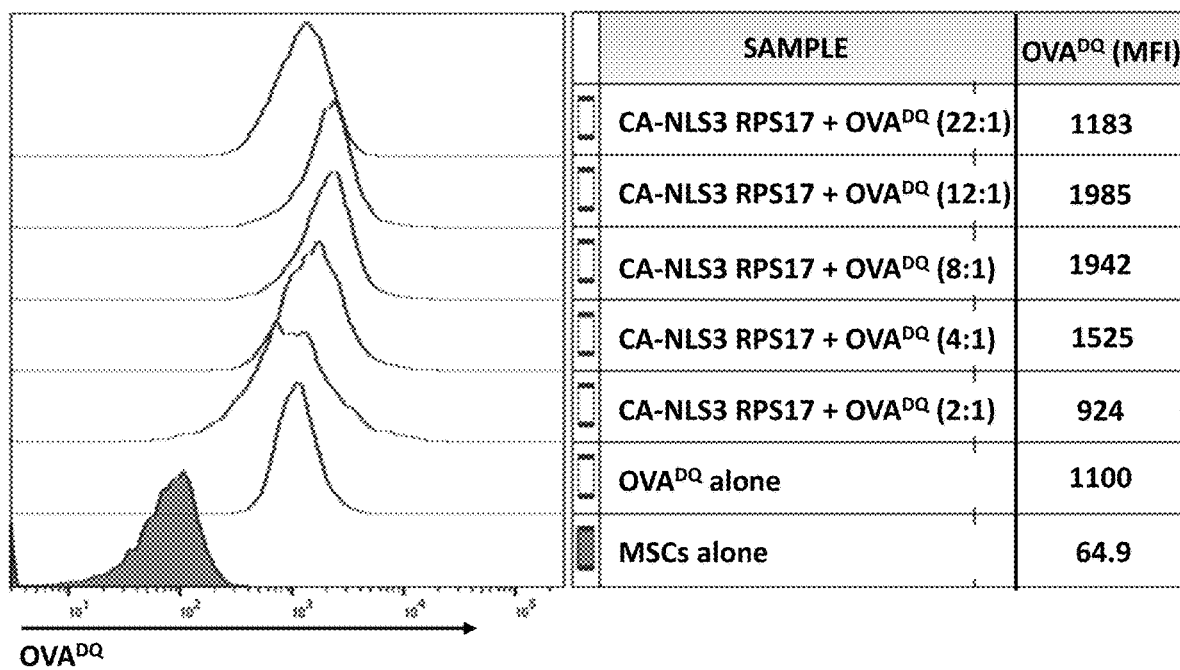
Figure 8C:
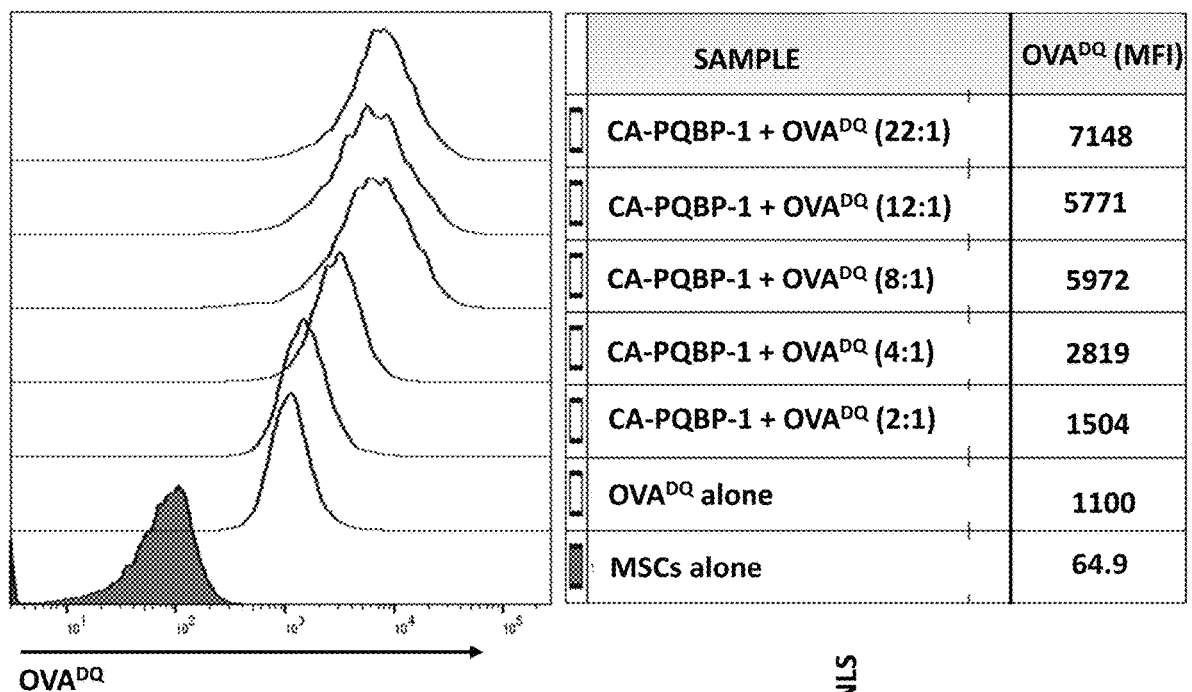
Figure 8D:
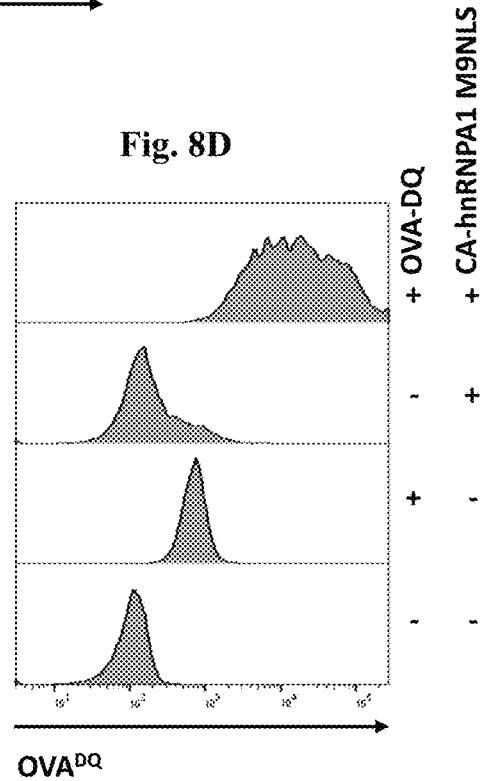

Using a cross-presenting cell line of MSCs as antigen presenting cells, various cholic acid peptide conjugates enhanced antigen presentation of OVA (FIG. 6). Similar to BMDCs, PQBP-1 NLS, HuR NLS, and GWG-SV40NLS were associated with strikingly high antigen-presentation activity, as compared to OVA alone or OVA mixed with CA-SV40NLS.

To further dissect the effect of bile acid peptide conjugates on antigen presentation, antigen internalization and processing were evaluated. MSC cell lines were pulsed with OVA-labelled with AF647 in the presence of various molar ratios of different bile acid peptide conjugates, NLS1-RPS17 [FIG. 7A]; NLS3 RPS17 [FIG. 7B]; PQBP-1 [FIG. 7C]; and hnRNPA1 M9 NLS [FIG. 7D]) and fluorescence was assessed by flow cytometry. Bile acid conjugates were shown to enhance OVA internalization, generally with increasing ratios. OVA processing was assessed by pulsing MSC cell lines with DQ™-Ovalbumin (OVA-DQ) in the presence of the same bile acid peptide conjugates as in FIGS. 7A to 7D. Bile acid conjugates NLS1-RPS17 [FIG. 8A]; NLS3 RPS17 [FIG. 8B]; PQBP-1 [FIG. 8C]; and hnRNPA1 M9 NLS [FIG. 8D]) were shown to enhance OVA processing, generally with increasing ratios.

In summary, these data demonstrate the versatility and capability of bile acid peptide conjugates in enhancing antigen presentation.

REFERENCES

Al-Hilal et al., (2014). Functional transformations of bile acid transporters induced by high-affinity macromolecules. *Scientific Reports*, 4: 4163. doi: 10.1038/srep04163.

Azuar et al., (2019). Cholic Acid-based Delivery System for Vaccine Candidates against Group A *Streptococcus*. *ACS Medicinal Chemistry Letters*, 10: 1253-1529.

Beaudoin et al., (2016). ChAcNLS, a novel modification to antibody-conjugates permitting target cell-specific endosomal escape, localization to the nucleus and enhanced total intracellular accumulation. *Molecular Pharmaceutics*, 13(6): 1915-26.

Hanafi et al., (2018). Overview of Bile Acids Signaling and Perspective on the Signal of Ursodeoxycholic Acid, the Most Hydrophilic Bile Acid, in the Heart. *Biomolecules*, 8(4): 159.

Liu et al., (2020), The Renpenning syndrome-associated protein PQBP1 facilitates the nuclear import of splicing factor TXNL4A through the karyopherin 2 receptor. *Journal of Biological Chemistry*, 295(13): 4093-4100.

Murakami et al., (2020). Bile acids and ceramide overcome the entry restriction for GII.3 human norovirus replication in human intestinal enteroids. *Proceedings of the National Academy of Sciences USA.* 117(3):1700-1710.

Patel et al., (2017). Next generation approaches for tumor vaccination. *Chinese Clinical Oncology.* 6(2):19.

Shivanna et al., (2014) The crucial role of bile acids in the entry of porcine enteric calicivirus. *Virology* 456-457, 268-278.

Shivanna et al., (2015). Ceramide formation mediated by acid sphingomyelinase facilitates endosomal escape of caliciviruses. *Virology*, 483, 218-228.

Smith et al., (2019). Alternative tumour-specific antigens. *Nature Review Cancer.* 19(8): 465-478.

Sun et al., (2016). Factors influencing the nuclear targeting ability of nuclear localization signals. *Journal of Drug Targeting*, 24(10): 927-933.

Tagliamonte et al., (2014). Antigen-specific vaccines for cancer treatment. *Human Vaccines & Immunotherapeutics*, 10(11): 3332-3346.

The invention claimed is:

1. A method of improving polypeptide antigen immunogenicity, the method comprising admixing a polypeptide antigen with an enhancer of antigen-presentation, the enhancer comprising a bile acid-peptide conjugate in an amount sufficient to improve presentation of the polypeptide antigen upon administration to antigen-presenting cells or to a subject, as compared to administration of a corresponding composition lacking the enhancer, wherein the peptide comprised in the bile acid-peptide conjugate comprises a nuclear localization signal (NLS).

2. The method of claim 1, wherein the bile acid is: cholic acid (CA), chenodeoxycholic acid (CDCA), deoxycholic acid (DCA), lithocholic acid (LCA), glycocholic acid (GCA), taurocholic acid (TCA), glycodeoxycholic acid (GDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA).

3. The method of claim 1, wherein the bile acid is an analog of CA, CDCA, DCA, LCA, GCA, TCA, GDCA, GCDCA, TDCA, GLCA, TLCA, THDCA, TCDCA, UCA, TUDCA, UDCA, or GUDCA, wherein the analog: induces endocytosis; triggers ceramide accumulation on the inner leaflet of endosomes; or triggers increased acid sphingomyelinase (ASM)-mediated cleavage of sphingomyelin to form ceramide.

4. The method of claim 1, wherein the bile acid is or comprises: glycodeoxycholic acid (GDCA), glycochenodeoxycholic acid (GCDCA), ursodeoxycholic acid (UDCA), or lithocholic acid (LCA).

5. The method of claim 1, wherein the NLS is a/an: SV40 NLS (SEQ ID NO: 1 or 2), GWG-SV4ONLS (SEQ ID NO: 3), hnRNPA1 M9NLS (SEQ ID NO: 4), hnRNP D NLS (SEQ ID NO: 5), hnRNP M NLS (SEQ ID NO: 10), PQBP-1 NLS (SEQ ID NO: 6), NLS2-RG Domain RPS17 (SEQ ID NO: 11), NLS1 RPS17 (SEQ ID NO: 15), NLS2 RPS17 (SEQ ID NO: 7), NLS3 RPS17 (SEQ ID NO: 8), cMyc NLS (SEQ ID NO: 12), HuR NLS (SEQ ID NO: 13), Tus NLS (SEQ ID NO: 14), or Nucleoplasmin NLS (SEQ ID NO: 16).

6. The method of claim 1, wherein the NLS is a variant of an NLS having nuclear localization activity, the NLS comprising or consisting of any one of the amino acid sequences consisting of any one of SEQ ID NOs: 1-8 and 10-16.

7. The method of claim 1, wherein the peptide is a non-immunogenic peptide.

8. The method of claim 1, wherein the peptide has a length of between 10 to 100 amino acids.

9. The method of claim 1, wherein the molar ratio of enhancer to antigen in the composition is between 1:1 to 1000:1.

10. The method of claim 1, wherein the molar ratio of enhancer to antigen in the composition is between 1:1 to 500:1.

11. The method of claim 1, wherein the molar ratio of enhancer to antigen in the composition is between 1:1 to 250:1.

12. The method of claim 1, wherein the antigen is a polypeptide antigen comprising one or more MHC class I epitopes and/or MHC class II epitopes.

13. The method of claim 1, wherein the polypeptide antigen is or comprises: a tumor-associated antigen (TAA), tumor-specific antigen (TSA), cell lysate derived from a tumor, tumor-derived exosomes, a neoantigen, a viral antigen, a bacterial antigen, a fungal antigen, or other antigen associated with a disease or disorder amenable to treatment by vaccination and/or immunotherapy.

14. The method of claim 1, wherein the polypeptide antigen is or comprises a SARS-CoV Spike protein or an antigenic fragment thereof.

15. The method of claim 1, wherein the enhancer enables:
    (i) increased cytosolic delivery of the antigen, as compared to a corresponding composition lacking the enhancer;
    (ii) increased total cellular delivery of the antigen, as compared to a corresponding composition lacking the enhancer;
    (iii) enhanced cellular immunity against the antigen, as compared to a corresponding composition lacking the enhancer;
    (iv) increased IFN-gamma production by CD8+T cells upon exposure to the antigen, as compared to a corresponding composition lacking the enhancer;
    (v) enhanced humoral immunity against the antigen, as compared to a corresponding composition lacking the enhancer;
    (vi) an increased variety of antibody species against the antigen, as compared to a corresponding composition lacking the enhancer; or
    (vii) any combination of (i) to (vi).

16. The method of claim 1, wherein the bile acid is cholic acid.

17. The method of claim 1, wherein the NLS is an hnRNPA1 M9 NLS (SEQ ID NO: 4).

18. The method of claim 1, wherein the bile acid is cholic acid and the NLS is an hnRNPA1 M9 NLS (SEQ ID NO: 4).

19. The method of claim 18, wherein the polypeptide antigen comprises cell lysate derived from a tumor.

20. The method of claim 19, wherein the enhancer enables enhanced cellular immunity against the antigen, as compared to a corresponding composition lacking the enhancer.

* * * * *

UNITED STATES PATENT AND TRADEMARK OFFICE
CERTIFICATE OF CORRECTION

| | | |
|---|---|---|
| PATENT NO. | : 11,612,651 B2 | Page 1 of 1 |
| APPLICATION NO. | : 17/738548 | |
| DATED | : March 28, 2023 | |
| INVENTOR(S) | : Simon Beaudoin | |

It is certified that error appears in the above-identified patent and that said Letters Patent is hereby corrected as shown below:

In the Claims

Column 24, Claim 5, Line 58:
"GWGW-SV4ONLS" should read: --GWG-SV40NLS--.

Signed and Sealed this
Twenty-first Day of January, 2025

Coke Morgan Stewart
*Acting Director of the United States Patent and Trademark Office*

SEQUENCE LISTING

<160> NUMBER OF SEQ ID NOS: 16

<210> SEQ ID NO 1
<211> LENGTH: 13
<212> TYPE: PRT
<213> ORGANISM: Artificial Sequence
<220> FEATURE:
<223> OTHER INFORMATION: SV40NLS

<400> SEQUENCE: 1

Cys Gly Tyr Gly Pro Lys Lys Lys Arg Lys Val Gly Gly
1               5                   10

<210> SEQ ID NO 2
<211> LENGTH: 7
<212> TYPE: PRT
<213> ORGANISM: Artificial Sequence
<220> FEATURE:
<223> OTHER INFORMATION: NLS from SV-40 large T-antigen

<400> SEQUENCE: 2

Pro Lys Lys Lys Arg Lys Val
1               5

<210> SEQ ID NO 3
<211> LENGTH: 19
<212> TYPE: PRT
<213> ORGANISM: Artificial Sequence

```
<220> FEATURE:
<223> OTHER INFORMATION: GWG-SV40NLS

<400> SEQUENCE: 3

Cys Gly Trp Trp Gly Tyr Gly Pro Lys Lys Arg Lys Val Gly Gly
1               5                   10                  15

Trp Trp Gly

<210> SEQ ID NO 4
<211> LENGTH: 20
<212> TYPE: PRT
<213> ORGANISM: Artificial Sequence
<220> FEATURE:
<223> OTHER INFORMATION: hnRNPA1 M9 NLS

<400> SEQUENCE: 4

Cys Ser Asn Phe Gly Pro Met Lys Gly Gly Asn Phe Gly Gly Arg Ser
1               5                   10                  15

Ser Gly Pro Tyr
            20

<210> SEQ ID NO 5
<211> LENGTH: 20
<212> TYPE: PRT
<213> ORGANISM: Artificial Sequence
<220> FEATURE:
<223> OTHER INFORMATION: hnRNP D NLS

<400> SEQUENCE: 5

Cys Ser Gly Tyr Gly Lys Val Ser Arg Arg Gly Gly His Gln Asn Ser
1               5                   10                  15

Tyr Lys Pro Tyr
            20

<210> SEQ ID NO 6
<211> LENGTH: 21
<212> TYPE: PRT
<213> ORGANISM: Artificial Sequence
<220> FEATURE:
<223> OTHER INFORMATION: PQBP-1 NLS

<400> SEQUENCE: 6

Cys Ala Asp Arg Glu Glu Gly Lys Glu Arg Arg His His Arg Glu
1               5                   10                  15

Glu Leu Ala Pro Tyr
            20

<210> SEQ ID NO 7
<211> LENGTH: 20
<212> TYPE: PRT
<213> ORGANISM: Artificial Sequence
<220> FEATURE:
<223> OTHER INFORMATION: NLS2 RPS17

<400> SEQUENCE: 7

Cys Asn Lys Arg Val Cys Glu Glu Ile Ala Ile Ile Pro Ser Lys Lys
1               5                   10                  15

Leu Arg Asn Lys
            20

<210> SEQ ID NO 8
<211> LENGTH: 19
<212> TYPE: PRT
<213> ORGANISM: Artificial Sequence
```

```
<220> FEATURE:
<223> OTHER INFORMATION: NLS3 RPS17

<400> SEQUENCE: 8

Ser Lys Lys Leu Arg Asn Lys Ile Ala Gly Tyr Val Thr His Leu Met
1               5                   10                  15

Lys Arg Ile

<210> SEQ ID NO 9
<211> LENGTH: 8
<212> TYPE: PRT
<213> ORGANISM: Artificial Sequence
<220> FEATURE:
<223> OTHER INFORMATION: SIINFEKL peptide

<400> SEQUENCE: 9

Ser Ile Ile Asn Phe Glu Lys Leu
1               5

<210> SEQ ID NO 10
<211> LENGTH: 20
<212> TYPE: PRT
<213> ORGANISM: Artificial Sequence
<220> FEATURE:
<223> OTHER INFORMATION: hnRNP M NLS

<400> SEQUENCE: 10

Cys Asn Glu Lys Arg Lys Glu Lys Asn Ile Lys Arg Gly Gly Asn Arg
1               5                   10                  15

Phe Glu Pro Tyr
            20

<210> SEQ ID NO 11
<211> LENGTH: 34
<212> TYPE: PRT
<213> ORGANISM: Artificial Sequence
<220> FEATURE:
<223> OTHER INFORMATION: NLS2-RG Domain RPS17

<400> SEQUENCE: 11

Cys Asn Lys Arg Val Cys Glu Glu Ile Ala Ile Ile Pro Ser Lys Lys
1               5                   10                  15

Leu Arg Asn Lys Gly Ser Gly Arg Ile Gln Arg Gly Pro Val Arg Gly
            20                  25                  30

Ile Ser

<210> SEQ ID NO 12
<211> LENGTH: 15
<212> TYPE: PRT
<213> ORGANISM: Artificial Sequence
<220> FEATURE:
<223> OTHER INFORMATION: cMyc NLS

<400> SEQUENCE: 12

Cys Gly Tyr Gly Pro Ala Ala Lys Arg Val Lys Leu Asp Gly Gly
1               5                   10                  15

<210> SEQ ID NO 13
<211> LENGTH: 22
<212> TYPE: PRT
<213> ORGANISM: Artificial Sequence
<220> FEATURE:
<223> OTHER INFORMATION: HuR NLS
```

```
<400> SEQUENCE: 13

Cys Gly Arg Phe Ser Pro Met Gly Val Asp His Met Ser Gly Leu Ser
1               5                   10                  15

Gly Val Asn Val Pro Gly
            20

<210> SEQ ID NO 14
<211> LENGTH: 15
<212> TYPE: PRT
<213> ORGANISM: Artificial Sequence
<220> FEATURE:
<223> OTHER INFORMATION: Tus NLS

<400> SEQUENCE: 14

Cys Gly Tyr Gly Lys Leu Lys Ile Lys Arg Pro Val Lys Gly Gly
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: NLS1 RPS17

<400> SEQUENCE: 15

Cys Met Gly Arg Val Arg Thr Lys Thr Val Lys Lys Ala Ala Gly Gly
1               5                   10                  15

<210> SEQ ID NO 16
<211> LENGTH: 21
<212> TYPE: PRT
<213> ORGANISM: Artificial Sequence
<220> FEATURE:
<223> OTHER INFORMATION: Nucleoplasmin NLS

<400> SEQUENCE: 16

Cys Ala Val Lys Arg Pro Ala Ala Thr Lys Lys Ala Gly Gln Ala Lys
1               5                   10                  15

Lys Lys Lys Leu Asp
            20
```